US012291725B2

(12) United States Patent
Ramaswamy et al.

(10) Patent No.: US 12,291,725 B2
(45) Date of Patent: May 6, 2025

(54) SYSTEMS AND METHODS FOR PRODUCING INJECTABLE ENHANCED STEM CELL EXOSOMES, IMPROVED EXOSOMES AND METHODS OF USE (71) Applicants: Sharan Ramaswamy, Miami, FL (US); Manuel Perez, Miami, FL (US); Yih-Mei Lin, Miami, FL (US)

(72) Inventors: Sharan Ramaswamy, Miami, FL (US); Manuel Perez, Miami, FL (US); Yih-Mei Lin, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/221,026

(22) Filed: Jul. 12, 2023

(65) Prior Publication Data
US 2023/0348860 A1 Nov. 2, 2023

Related U.S. Application Data (62) Division of application No. 17/119,170, filed on Dec. 11, 2020, now Pat. No. 11,746,329.

(60) Provisional application No. 62/947,379, filed on Dec. 12, 2019.

(51) Int. Cl.
C12N 5/0775 (2010.01)
A61K 9/00 (2006.01)
A61K 35/28 (2015.01)
A61P 9/10 (2006.01)
C07K 14/47 (2006.01)
C07K 14/765 (2006.01)

(52) U.S. Cl.
CPC .......... C12N 5/0663 (2013.01); A61K 9/0019 (2013.01); A61K 35/28 (2013.01); A61P 9/10 (2018.01); C07K 14/47 (2013.01); C07K 14/4717 (2013.01); C07K 14/765 (2013.01); C12N 2521/00 (2013.01); C12N 2533/40 (2013.01); C12N 2533/92 (2013.01)

(58) Field of Classification Search
CPC .... C12N 5/0663; A61K 9/0019; A61K 35/28; A61P 9/10; C07K 14/47; C07K 14/4717
See application file for complete search history.

(56) References Cited

U.S. PATENT DOCUMENTS 10,488,403 B2 * 11/2019 Ghosh ............... B01J 20/28009
2017/0360840 A1 * 12/2017 Hogan ............ C12Y 306/01003
2018/0147241 A1 * 5/2018 Matheny ............... A61K 35/34

OTHER PUBLICATIONS

Bakhtyar et al. Exosomes from acellular Wharton's jelly of the human umbilical cord promotes skin wound healing Stem Cell Research & Therapy (2018) 9:193 (Year: 2018).*
Vrijsen et al. Exosomes from Cardiomyocyte Progenitor Cells and Mesenchymal Stem Cells Stimulate Angiogenesis via EMMPRIN Adv. Healthcare Mater. 2016, 5, 2555-2565 (Year: 2016).*
Vrijsen et al. Cardiomyocyte progenitor cell-derived exosomes stimulate migration of endothelial cells, J. Cell. Mol. Med. vol. 14, No. 5, 2010 pp. 1064-1070 (Year: 2010).*
Lai et al. Proteolytic Potential of the MSC Exosome Proteome: Implications for an Exosome-Mediated Delivery of Therapeutic Proteasome, International Journal of Proteomics vol. 2012, Article ID 971907, 14 pages (Year: 2012).*
Cha, Jae Min et al. "Efficient scalable production of therapeutic microvesicles derived from human mesenchymal stem cells." Scientific Reports, 8(1):1-23, Jan. 19, 2018.
Egger, Dominik et al. "Dynamic Cultivation of Mesenchymal Stem Cell Aggregates." Bioengineering 5(48):1-15, Jun. 19, 2018.
Gallet, Romain et al. "Exosomes secreted by cardiosphere-derived cells reduce scarring, attenuate adverse remodelling, and improve function in acute and chronic porcine myocardial infarction." European Heart Journal 38 (3):201-211, (Year: 2017).
Ramaswamy, Sharan "A Novel Bioreactor for Mechanobiological Studies of Engineered Heart Valve Tissue Formation Under Pulmonary Arterial Physiological Flow Conditions." Journal of Biomechanical Engineering 136(12):1-14, Dec. 2014.
Rath, Sasmita et al. "Differentiation and Distribution of Marrow Stem Cells in Flex-Flow Environments Demonstrate Support of the Valvular Phenotype." PloS one 10(11):1-19, Nov. 4, 2015.
Teng, Xiaomei et al. "Mesenchymal Stem Cell-Derived Exosomes Improve the Microenvironment of Infarcted Myocardium Contributing to Angiogenesis and Anti-Inflammation." Cell Physiol Biochem 37(6):2415-2424, (Year: 2015).
Williams, A. et al. "A "Sweet-Spot" for Fluid-Induced Oscillations in the Conditioning of Stem Cell-based Engineered Heart Value Tissues." Journal of Biomechanics 65:40-48, (Year: 2017).

* cited by examiner

Primary Examiner — Maria G Leavitt
Assistant Examiner — Alexandra F Connors
(74) Attorney, Agent, or Firm — SALIWANCHIK, LLOYD & EISENSCHENK (57) ABSTRACT This disclosure pertains to a non-living biological product. Particularly, exosomes derived from stem cells can help restore heart function. According to certain embodiments, a fluid-induced shear stress mechanical stimulation process of stem cells is used to augmented quantity and quality of exosomes produced from stem cells. These exosomes serve as a therapeutic agent for the regenerative repair of diseases, such as diseased heart tissues. Therefore, compositions comprising the exosomes derived from stem cells and methods of treating a degenerative disease by administering the exosomes isolated from stem cells are also provided.

5 Claims, 5 Drawing Sheets

SYSTEMS AND METHODS FOR PRODUCING INJECTABLE ENHANCED STEM CELL EXOSOMES, IMPROVED EXOSOMES AND METHODS OF USE

CROSS-REFERENCE TO A RELATED APPLICATION

This application is a divisional application of co-pending application Ser. No. 17/119,170, filed Dec. 11, 2020, which claims the benefit of U.S. provisional application Ser. No. 62/947,379, filed Dec. 12, 2019, all of which are incorporated herein by reference in its entirety.

BACKGROUND

Heart disease is the leading cause of death for both men and women in the United States. Coronary heart disease is the most common type of heart disease. Every year approximately 790,000 Americans have a heart attack, resulting in over 370,000 deaths per year. In coronary artery disease, the arteries that supply blood to the heart become occluded due to plaque build-up in the arterial walls. If the obstruction is severe enough, it can prevent blood from reaching portions of the heart muscle, resulting in myocardial infarction (MI), leading to irreversible damage and necrosis of the heart tissue. The resulting cardiomyopathy produces scar tissue in the affected muscles, inhibiting the heart's ability to properly pump blood, which in turn can lead to heart failure. Although current medical devices such as stents and vascular grafts provide effective management to a sub-set of patients, they have distinct limitations and, importantly, do not restore the health of cardiac tissues that have already been damaged by a heart attack.

Current treatments for ischemic cardiomyopathy focus on minimizing the existing post-infarct damage to the myocardium and avoiding further progression of fibrotic lesions. Nonetheless, the initial lesion persists, and the subsequent formation of non-contractile fibrotic tissue leads to infarct expansion and extension, which reduces the functional capacity of the heart and can lead to heart failure. The use of stem cells as a therapeutic strategy for the treatment of cardiac diseases has emerged in the last two decades. The potential for treating ischemic cardiomyopathy via neovascularization of the heart thereby leading to regeneration of myocardial tissues has been the driving force of these stem cell investigations.

Recently, stem cell-injection therapy has been investigated as an option to treat the infarcted myocardium with the goal of regenerating cardiac muscle and restoring heart function. Over 244 clinical trials have been initiated to explore the use of stem cells to treat ischemic cardiomyopathy. Mesenchymal stem cells (MSCs) such as bone marrow mesenchymal stem cells (BMSCs) are considered to hold great therapeutic value for cell-based therapies and tissue regeneration. Numerous preclinical studies of ischemic cardiomyopathy employing an MSC-based therapy have demonstrated that fibrosis, i.e., scar tissue reduction and stimulating cardiomyogenesis, can lead to improvements in the structure and function of remodeled ventricles. Scientists have used the implantation of human, adult BMSCs and human adult cardiac stem cells (CSCs) to induce remodeling and regeneration of affected tissue. However, the use of undifferentiated mesenchymal stem cells has produced only marginal results due to their poor retention and engraftment in the diseased tissue.

As another example, allogeneic BMSCs that were intravenously delivered in baboons (2 million cells/kg-body-weight) immediately following induced MI, exhibited neovascularization and capillarization within the cardiac tissues, post-treatment. While these beneficial effects have been reported, the underlying mechanisms are not well understood. It has been observed that after injection into the heart, exogenous MSCs show poor survival and engraftment into the infarct site, with evidence that MSCs do not persist and disappear 4 weeks after transplantation. This suggests that instead of direct differentiation of MSCs, other secondary or trophic effects are involved in producing the observed benefits.

CSCs have recently showed more favorable results in treating ischemic cardiac diseases. These cells are isolated via biopsies of the heart muscle but are present in the tissue in very low numbers. In addition, being adult stem cells, the expansion potential for these cells is very limited. The result of these barriers is that CSCs are very costly and in limited supply. This is a major pain point in the stem cell market in that the best performing cells for treatment of ischemia-induced cardiac tissue damage are basically unavailable for use in commercial scale applications.

Thus, there is a need for a product that can replicate the benefits of adult CSCs, while being available in sufficient quantities and at reasonable costs of production. This disclosure aims to deliver a therapeutic from exosomes derived from stem cells that can help restore heart function.

BRIEF DESCRIPTION OF THE INVENTION

The subject invention pertains to bioreactors that provide pulsatile fluid-induced oscillatory shear stresses to the stem cells cultured in the bioreactors to mechanically stimulate the stem cells to produce and subsequently release into the culture media exosomes in relatively high quality and concentration. In preferred embodiments, the bioreactor is modified to permit a conditioning chamber to house a cylindrical bio-scaffold sleeve. A substantially higher number of stem cells can be seeded onto the larger sleeve surface area (about 1 million cells/$cm^2$, for example, on the side exposed to flow), and then oscillatory flow-conditioned, to further augment the number of exosomes released into the culture media.

In one embodiment, the subject invention provides a method for producing secreted exosomes of stem cells, the method comprising culturing the stem cells in a bioreactor comprising a pulsatile flow pump that delivers dynamic flow conditions to the cultured stem cells, and isolating the secreted exosomes. In one embodiment, the bioreactor comprises the pulsatile flow pump that delivers oscillatory flow conditions relevant to the cardiovascular system, wherein the oscillatory flow conditions relevant to the cardiovascular system have, for example, a shear index/OSI of about 0.2.

In one embodiment, culturing the stem cells in the bioreactor comprises seeding the stem cells on a bio-scaffold, placing the bio-scaffold in the bioreactor, and culturing the stem cells under a static and/or dynamic flow condition. In a further embodiment, the bio-scaffold comprises PSIS or PGA-PLLA.

The subject invention also provides a mechanically conditioned 3-D cell culture system, and a composition comprising secreted exosomes of bone marrow mesenchymal stem cells (BMSCS) or cardiac stem cells (CSCs) for use as a therapeutic agent for the regenerative repair of diseased heart tissues. Advantageously, because exosomes are non-living, the need to prolong stem cell survival in the heart would be eliminated. These exosomes comprise a cocktail of molecular factors that promote cardiac function via neovascularization and de novo tissue formation. In a preferred embodiment, the secreted exosomes of stem cells comprise one or more cardiac tissue-specific proteins selected from serum albumin, serotransferrin, and alpha-2-macroglobulin.

In a specific embodiment, a composition of the subject invention comprises injectable enhanced stem cell exosomes (IESCE).

In a preferred embodiment, exosomes or IESCE are derived from statically cultured, adult, human BMSCs, from physiologically-relevant, oscillatory flow conditioned adult, human BMSCs, and/or from statically cultured, adult, human cardiac stem cells (CSCs) which have been shown to release potent factors beneficial for cardiac regeneration.

In one embodiment, the composition and/or secreted exosomes of the subject invention comprise an increased amount of total proteins and a minimal amount of fibronectin.

Further embodiments of the invention also provide methods of treating a degenerative disease, such as cardiovascular disease (e.g., myocardial infarction), by administering to a subject a composition comprising secreted exosomes obtained from stem cells cultured under pulsatile fluid-induced oscillatory shear stresses. The stem cells can be BMSCs or CSCs.

In one embodiment, the subject invention also provides a method for promoting cardiac tissue regeneration, the method comprising identifying a damaged cardiac tissue in a subject, and administering to the subject the composition or secreted exosomes of the subject invention. In a preferred embodiment, the administration is via intra-cardiac injection.

In preferred embodiments, IESCE accelerate healing and remodeling responses of cardiovascular structure (e.g., heart, blood vessels, or heart valve) damaged from disease. Furthermore, the bioreactor's ability to mimic the human circulation facilitates the production of an "off-the-shelf" system that has broader use beyond regenerative medicine (e.g. in cardiovascular drug discovery).

BRIEF DESCRIPTION OF DRAWINGS

FIG. 2. A design modification to simplify oscillatory flow bioreactor conditioning chamber (annulus flow design). A bio-scaffold sleeve is secured onto a cylindrical mandrel while flow is permitted in the annular region between the mandrel and inner tube. The end-result will be that a much higher density (compared to scaffold strips) of seeded cells can be mechanically-conditioned via oscillatory flow, to release a potent concentration of IESCE, which can subsequently be isolated from the conditioned media.

FIGS. 3A-3C. Gene expression of BMSCs exposed to low OSI (OSI=0.10), high OSI (OSI=0.38) and physiologically relevant OSI (OSI=0.23). (3A) A statistically significant ($p<0.05$) expression of CD31, a-SMA was found in the physiologically relevant OSI-treated group as compared to the low and high OSI counterparts. (3B) A significantly higher expression ($p<0.05$) of BMP2 was also observed in the physiologically-relevant OSI groups as compared to the other two groups. No significant differences ($p>0.05$) were found in the expression of osteocalcin between the groups. (3C) KLF2A and NOTCH1 genes exhibited a significantly higher expression ($p<0.05$) in the physiologically relevant OSI group. Finally, TGFβ1 was significantly down-regulated in the low OSI and physiologically relevant groups ($p<0.05$) in comparison to high OSI-treatment wherein it was upregulated. These findings thus identify a simple yet highly-specific mechanical conditioning protocol using physiologically-relevant pulsatile flow-alone that permits BMSCs to differentiate in vitro towards the cardiovascular-relevant phenotypes. Moreover, BMSC-derived trophic molecular factors are likely to accelerate healing, tissue remodeling and growth potential in vivo.

DETAILED DESCRIPTION

The subject invention provides products and compositions for use as therapeutic agents for restoring heart function, regenerating heart tissue, and/or treating degenerative diseases, for example, cardiovascular diseases. Advantageously, the products and compositions of the subject invention can replicate the benefits of adult cardiac stem cells (CSCs).

The subject invention also provides methods of producing the products and compositions using a mechanically conditioned 3-D cell culture system. The subject invention further provides methods of using the compositions and products for restoring heart function, regenerating heart tissue, and/or treating degenerative diseases.

In one embodiment, the composition comprises secreted exosomes of stem cells such as bone marrow stem cells and CSCs. Preferably, the BMSCs are bone marrow mesenchymal stem cells (BMSCs).

Exosomes are nanometer-sized membrane-bound vesicles (e.g., 40-150 nm) containing, for example, cytokines and growth factors, lipids, mRNAs, and regulatory miRNAs. Exosomes contain a conserved set of proteins including tetraspanins (e.g., CD81, CD63, and CD9), heat-shock proteins (e.g., HSP60, HSP70 and HSP90), targeting or adhesion markers such as integrins, ICAM-1, EpCAM, membrane fusion markers such as annexins, tumor susceptibility gene 101 (TSG101), and ALIX; and may also contain unique tissue-specific proteins that reflect their cellular origins.

The principal mode of action of MSCs is the localized production and secretion of bioactive trophic factors. The predominant method by which stem cells facilitate healing of cardiovascular tissues is via the release of trophic factors that lead to paracrine-mediated events thereby inducing regeneration. Therefore, stem cells are not required to promote repair; rather the factors that they release in a physiologically-relevant and mechanically active environment are solely needed.

The term "mesenchymal stem cell" or "MSC", as used herein, refers to a multipotent somatic stem cell derived from mesoderm, having self-regenerating and differentiating capacity to produce progeny cells with a large phenotypic variety, including connective tissues, stroma of bone marrow, adipocytes, dermis and muscle, among others. MSCs may be isolated from any type of tissue. Generally, MSCs may be isolated from bone marrow, adipose tissue, umbilical cord, or peripheral blood. In a particular embodiment, the MSC are bone marrow-derived stem cells.

"Bone marrow mesenchymal stem cells," or "bone marrow derived mesenchymal stem cells" refer to cells existing in the bone marrow, which can be directly collected from the bone marrow or indirectly collected from other tissues (e.g., blood, skin, fat, and other tissues), and can be cultured and proliferated as adherent cells on a solid surface, e.g., a culture dish (made of plastic or glass). These cells are characterized in having a potential to differentiate into mesenchymal tissues such as bone, cartilage, and fat, or into skeletal muscle, heart muscle, nervous tissues, and epithelial tissues, and can be obtained by collection of bone marrow cells. Markers for human bone marrow mesenchymal stem cells can be, for example, all or some of the following, but are not limited to, Lin-negative, CD45-negative, CD44-positive, CD90-positive, and CD29-positive.

Specific physiologically-relevant mechanical conditions were identified that can be created using bioreactors to produce injectable enhanced stem cell exosomes (IESCE). IESCE can be delivered without a living cellular component, thus reducing concerns associated with contamination risk and hostile immune responses. Secondly, storage and transportation of liquid media containing potent healing factors, such as our proposed IESCE-product, for optimal delivery in a clinical setting would be more straightforward and inexpensive compared to directly using the cells themselves, which would thereby allow the manufacturing at-scale of this therapeutic.

Analyses of MSC conditioned medium indicates that MSCs secrete mediators of tissue repair, including growth factors, cytokines and chemokines. These factors provide the paracrine signaling and cell-cell interactions that stimulate native parenchymal cells to initiate repair of damaged issues. This signaling regulates an array of regenerative functions such as modulating the local immune system, enhancing angiogenesis, preventing cell apoptosis as well as stimulating survival, proliferation and differentiation of resident tissue-specific cells.

Key cardiac repair factors released by MSCs include vascular endothelial growth factor (VEGF), transforming growth factor beta 1 (TGF-β1), fibroblast growth factor 2 (FGF-2), hepatocyte growth factor (HGF) and granulocyte colony stimulating factor (G-CSF). With the secretion of growth factors, extracellular vesicles and exosomes, MSCs act to promote specific biological activities by native progenitor cells that can lead to cardiac tissue repair.

Specific biomechanical fluid-induced stress conditions were identified that permit scaffold-seeded human BMSCs to secrete augmented biological factors into the culture media that promote de novo cardiovascular ECM formation. These factors can be isolated and delivered to damaged heart tissues as an injectable therapeutic.

The exosomes can comprise a cocktail of molecular factors that promote cardiac function via neovascularization and de novo tissue formation. Accordingly, certain embodiments of the invention provide IESCE that could be used to treat a heart disease. IESCE accelerates healing and remodeling responses of cardiovascular structures (e.g., heart, blood vessels, and heart valve) damaged from disease.

In one embodiment, the composition comprises IESCE and a pharmaceutically acceptable carrier. In a further embodiment, the composition is cell-free. "Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

IESCE can be produced in commercially adequate quantities thereby overcoming supply limitations of CSCs. The IESCE, which comprise non-living trophic factors, will induce cardiac tissue regeneration and thereby not require the extended stem cell survival that limits cell-based cardiac therapies.

IESCE can be derived from: (i) statically cultured, adult, human BMSCs (ii) physiologically-relevant, oscillatory flow-conditioned adult, human BMSCs or (iii) statically cultured, adult, human cardiac stem cells (CSCs) which have shown to release potent factors beneficial for cardiac regeneration. Note that the IESCE is a non-living biological product and hence lends itself to repeat ability in manufacturing at a large-scale, as an off-the-shelf therapeutic.

In one embodiment, the compositions of subject invention or the secreted exosomes of the subject invention, e.g., IESCE, comprise tissue repair factors including vascular endothelial growth factor (VEGF), interleukin-6 (IL-6), IL-10, transforming growth factor beta 1 (TGF-β1), fibroblast growth factor 2 (FGF-2), extracellular matrix metalloproteinase inducer (EMMPRIN), MMP-9, hepatocyte growth factor (HGF) and granulocyte colony stimulating factor (G-CSF).

In one embodiment, the compositions of the subject invention or the secreted exosomes comprise one or more cardiac tissue-specific proteins such as serum albumin, serotransferrin, and alpha-2-macroglobulin.

In one embodiment, the compositions of the subjection invention or the secreted exosomes of the subject invention comprise a significant increased amount of total proteins compared to that from a control condition. The increase in total protein quantity in secreted exosomes according to the subject invention can be about a 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 110%, 120%, 150%, 200%, 250%, 280%, 300%, 350%, 400%, 450%, 500%, 600%, 700%, 800%, 900%, 1000%, 2000%, 3000%, 4000%, 5000% or more, or any amount of increase in between.

In one embodiment, the exosomes, i.e., IESCE, secreted from stem cells comprises a total protein of at least 1.5 ng/cell, at least 2 ng/cell, at least 2.5 ng/cell, at least 3 ng/cell, at least 3.5 ng/cell, at least 4 ng/cell, at least 4.5 ng/cell, at least 5 ng/cell, at least 5.5 ng/cell, at least 6 ng/cell, at least 6.5 ng/cell, at least 7 ng/cell, at least 7.5 ng/cell, at least 8 ng/cell, at least 8.5 ng/cell, at least 9 ng/cell, at least 9.5 ng/cell, at least 10 ng/cell, at least 11 ng/cell, at least 12 ng/cell, at least 13 ng/cell, at least 14 ng/cell, at least 15 ng/cell, at least 16 ng/cell, at least 17 ng/cell, at least 18 ng/cell, at least 19 ng/cell, at least 20 ng/cell, at least 21 ng/cell, at least 22 ng/cell, at least 23 ng/cell, at least 24 ng/cell, at least 25 ng/cell, at least 26 ng/cell, at least 27 ng/cell, at least 28 ng/cell, at least 29 ng/cell, at least 30 ng/cell, at least 35 ng/cell, at least 40 ng/cell, at least 45 ng/cell, at least 50 ng/cell, at least 55 ng/cell, at least 60 ng/cell, at least 65 ng/cell, at least 70 ng/cell, at least 75 ng/cell, at least 80 ng/cell, at least 85 ng/cell, at least 90 ng/cell, at least 95 ng/cell, at least 100 ng/cell, or any amount in between.

In one embodiment, the composition of the subject invention may further comprise non-exosome components from the culture media, wherein the non-exosome components are secreted from the stem cells in culture. In one embodiment, the non-exosomes components may comprise a total protein of at least 1.5 ng/cell, at least 2 ng/cell, at least 2.5 ng/cell, at least 3 ng/cell, at least 3.5 ng/cell, at least 4 ng/cell, at least 4.5 ng/cell, at least 5 ng/cell, at least 5.5 ng/cell, at least 6 ng/cell, at least 6.5 ng/cell, at least 7 ng/cell, at least 7.5 ng/cell, at least 8 ng/cell, at least 8.5 ng/cell, at least 9 ng/cell, at least 9.5 ng/cell, at least 10 ng/cell, at least 11 ng/cell, at least 12 ng/cell, at least 13 ng/cell, at least 14 ng/cell, at least 15 ng/cell, at least 16 ng/cell, at least 17 ng/cell, at least 18 ng/cell, at least 19 ng/cell, at least 20 ng/cell, at least 21 ng/cell, at least 22 ng/cell, at least 23 ng/cell, at least 24 ng/cell, at least 25 ng/cell, at least 26 ng/cell, at least 27 ng/cell, at least 28 ng/cell, at least 29 ng/cell, at least 30 ng/cell, at least 35 ng/cell, at least 40 ng/cell, at least 45 ng/cell, at least 50 ng/cell, at least 55 ng/cell, at least 60 ng/cell, at least 65 ng/cell, at least 70 ng/cell, at least 75 ng/cell, at least 80 ng/cell, at least 85 ng/cell, at least 90 ng/cell, at least 95 ng/cell, at least 100 ng/cell, or any amount in between.

In one embodiment, the compositions of the subjection invention comprise a significant increased amount of total proteins from the non-exosome components compared to that from a control condition. The increase in total protein quantity in non-exosome components according to the subject invention can be about a 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 110%, 120%, 150%, 200%, 250%, 280%, 300%, 350%, 400%, 450%, 500%, 600%, 700%, 800%, 900%, 1000%, 2000%, 3000%, 4000%, 5000% or more, or any amount of increase in between.

In a specific embodiment, the compositions of the subject invention or the secreted exosomes comprise a significant reduced amount of fibronectin compared to that from a control condition. The reduction in fibronectin quantity in secreted exosomes and/or the composition according to the subject invention can be about a 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 100%, or any amount of reduction in between.

It is advantageous that the IESCE and/or the composition of the subject invention comprise a significantly reduced amount of fibronectin because overexpression of fibronectin could be harmful to a diseased heart (e.g., myocardial infarction and atherosclerosis), for example, by contributing to cardiac fibrosis. In one embodiment, the composition is formulated in accordance with routine procedures as a pharmaceutical composition adapted for local administration to, for example, humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form. Where the composition is administered by injection, an ampoule of sterile water for injection or saline can be provided so that the ingredients may be mixed prior to administration.

The pharmaceutical compositions may be formulated in any forms that are suitable for parenteral administration, including solutions, suspensions, liposomes, microspheres, and nanosystems suitable for solutions or suspensions in liquid prior to injection.

The compositions of the present invention can be administered to the subject being treated by standard routes, including the local, oral, ophthalmic, nasal, topical, transdermal, intra-articular, parenteral (e.g., intravenous, intraarterial, intraperitoneal, intrathecal, intraventricular, intradermal, intracavity, subcutaneous or intramuscular), intracranial, intracerebral, intraspinal, intrauterine, or rectal route. Depending on the condition being treated, one route may be preferred over others, which can be determined by those skilled in the art. Preferably, the composition is administered by injection (e.g., IV injection), gradual infusion over time or implantation.

Depending on the route of administration, the pharmaceutical composition can be associated with a material to protect the pharmaceutical composition from the action of enzymes, acids, and other natural conditions that may inactivate the pharmaceutical composition. Dispersions can also be prepared in glycerol, liquid polyethylene glycols, and mixtures thereof, and in oils. Under ordinary conditions of storage and use, these preparations may contain a preservative to prevent the growth of microorganisms.

Administration can be carried out using therapeutically effective amounts of the agents described herein for periods of time effective according to the subject invention.

In one embodiment, the pharmaceutical composition comprising secreted exosomes of stem cells according to the invention, together with an adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same.

In one embodiment, the composition of the subject invention may further comprise a therapeutic agent. Preferably, the therapeutic agent comprises one or more cytokines, drugs, nucleic acids, small molecules, or proteins that can be used for treating cardiovascular diseases.

In one embodiment, the subject invention pertains to a bioreactor that, via pulsatile fluid-induced oscillatory shear stresses, can mechanically stimulate stem cells to produce and subsequently release into the culture media exosomes in relatively high quality and concentration. Certain examples of bioreactors that could be used in the methods used in this disclosure are described in the U.S. Pat. No. 8,852,923, which is incorporated herein by reference in its entirety.

Certain embodiments of the subject invention also provide a mechanically conditioned 3-D cell culture system. The bioreactor's ability to mimic the human circulation enables the possibility of an "off-the-shelf" system which has broader use beyond regenerative medicine (e.g., in cardiovascular drug discovery).

In one embodiment, the mechanically conditioned 3-D cell culture system comprises a bioreactor comprising a separable and insertable cylindrical bio-scaffold sleeve or cylindrical specimen holder in a chamber of the bioreactor, wherein the chamber is in fluidic communication with culture media flow that is facilitated by a programmable pulsatile pump system. In a specific embodiment, a substantially higher number of stem cells can be seeded onto the larger sleeve surface area (about 1 million cells/cm$^2$, for example, on the side exposed to flow), and then oscillatory flow-conditioned, to further augment the number of exosomes released into the culture media.

In one embodiment, the cylindrical specimen holder comprises an inner tube connected to an inlet tube for receiving the culture media and an outlet tube for, e.g., exporting the culture media, a mandrel to secure the bio-scaffold, and an outer tube covering the inner tube and optionally, the inlet tube and outlet tube.

In a preferred embodiment, the bio-scaffold sleeve is secured onto a cylindrical mandrel while flow is permitted in the annular region between the mandrel and inner tube. A much higher density of seeded cells can be mechanically-conditioned via oscillatory flow, to release a potent concentration of IESCE, which can subsequently be isolated from the conditioned media.

In one embodiment, the 3-D culture system further comprises other components including tubes, glass media bottles, flow probes, pressure sensors and test software used to obtain the hydrodynamic data during the flow and pressure testing phase.

Stem cell-injection therapy to the heart has been investigated for the treatment of cardiovascular diseases. However, recent research has shown that the role of implanted stem cells is not for the cells to produce new ECM, but to initiate paracrine signaling that would regulate native cardiac cells to promote restoration of heart function. These trophic effects can, in essence, be replicated by IESCE without the need to inject live cell products that require specialized handling and storage. IESCE is a non-living entity, can be manufactured in scale, is easily stored and avoids the availability and cost issues associated with CSCs. In accordance with the subject invention, IESCE can be produced in unlimited quantities to improve cardiac function, thereby overcoming supply limitations of CSCs. The IESCE, which is comprised of non-living trophic factors, induces cardiac tissue regeneration and thereby not require the extended stem cell survival that limits cell-based cardiac therapies.

The secretion factors of CSC's have a powerful cardio-protective effect in the ischemic myocardium. Paracrine factors released from transplanted CSCs lead to cardiac repair, thereby contributing towards improved and sustainable cardiac function. The cardio preservative benefits of transplanted CSCs can be attributed to the powerful paracrine effects from the release of their exosomes that activate resident stem cells. Furthermore, the secreted factors presented in the cell conditioning medium have also been shown to improve tissue repair.

Importantly, CSC-secreted exosomes contain key cardio-protective proteins, lipids and genetic material, which can recapitulate the cardio-reparative effects of CSCs when injected into the infarcted myocardium. Of particular note, when injected in animal hearts, the cell-free conditioned media containing the released CSC exosomes has shown cardio-reparative effects equivalent to transplanting the cells, with implications on how an exosome-containing IESCE could be applied to treat ischemic cardiomyopathy.

Administration of cell-free IESCE therapy can provide cardio-reparative effects by activating the paracrine signaling loop in endogenous resident stem cells, which in turn may act as regenerative effectors in situ.

In one embodiment, the method according to the subject invention comprising collecting the secreted paracrine factors in the spent culture medium of pulsatile-flow conditioned BMSCs, i.e., IESCE. These factors can act as trophic mediators that upon injection to the damaged myocardium, can lead to accelerated restorative effects.

Notably BMSCs are directly being used to treat the damaged heart muscle via injection therapy but as their survival in heart tissues is extremely limited, so are their effects. The IESCE, a non-living biologic, is to thus leverage the beneficial effects of BMSC injections into the damaged heart muscle in a manner that is not cell survival-dependent, thereby enabling further restoration of heart function.

In one embodiment, these factors include, but are not limited to growth factor, cytokines and chemokines. These factors provide the paracrine signaling and cell-cell interactions that stimulate native parenchymal cells to initiate repair of damaged tissues. This signaling regulates an array of regenerative functions such as modulating the local immune system, enhancing angiogenesis, preventing cell apoptosis as well as stimulating survival, proliferation and differentiation of resident tissue-specific cells. Key cardiac repair factors released by MSCs include vascular endothelial growth factor (VEGF), transforming growth factor beta 1 (TGF-β1), fibroblast growth factor 2 (FGF-2), hepatocyte growth factor (HGF) and granulocyte colony stimulating factor (G-CSF). With the secretion of growth factors, extracellular vesicles and exosomes, MSCs act to promote specific biological activities by native progenitor cells that can lead to cardiac tissue repair.

In one embodiment, the bioreactor is modified to permit the conditioning chamber to house a cylindrical bio-scaffold sleeve. A substantially higher number of stem cells can be seeded onto the much larger sleeve surface area (about 1 million cells/cm$^2$, for example, on the side exposed to flow), and then oscillatory flow-conditioned, to further augment the number of exosomes released into the culture media.

The bioreactor can deliver oscillatory flow conditions of relevance to the cardiovascular system (an oscillatory shear index/OSI, for example, of roughly 0.2). Conditioning of stem cells on a bioscaffold substrate for a period of 2 weeks at this physiologically-relevant oscillatory shear stress and directionality (3-5 dynes/cm2; OSI=0.2), after an initial 8 day static culture period will lead to the secretion of IESCE into the media. Finally, centrifugation and precipitation-based exosome isolation procedures followed by filtration steps will yield IESCE.

In one embodiment, the subject invention provides a method of producing secreted exosomes (e.g., IESCEs) from cells, preferably stem cells, such as MSCs and CSCs, the method comprising culturing the cells in a bioreactor system, wherein the bioreactor system comprises one or more bioreactors and the cells are cultured in the bioreactors separately or sequentially in culture medium; collecting the culture medium from the bioreactor system; and isolating exosomes from the culture medium.

The term "bioreactor" can refer to a large-scale cell culture system that provides nutrients to cells and removes metabolites, as well as furnishes a physio-chemical environment conducive to cell growth, in a closed sterile system. In specific embodiments, the biological processes (e.g., secretion of exosomes) develop under monitored and controlled environmental and operating conditions, for example, pH, temperature, pressure, nutrient supply and waste removal. Examples of bioreactors include, but are not limited to, static bioreactor, stirred flask bioreactor, rotating bioreactor, and direct perfusion bioreactor.

In one embodiment, the bioreactor is a flow perfusion bioreactor system that comprises a pulsatile flow pump that provides controlled flow conditions (static and dynamic, e.g., pulsatile and/or oscillatory flow) to the cultured cells.

In specific embodiments, the bioreactor comprises a separable and insertable cylindrical specimen holder, one or more U-shaped bioreactor chambers that house the cell-seeded scaffolds, wherein the bioreactor chambers are in fluidic communication with culture media flow that is facilitated by a programmable pulsatile pump system. In one embodiment, the scaffolds can be placed in each bioreactor chamber in a parallel configuration to the flow direction and fully immersed in the media solution. In some embodiments, the flow perfusion bioreactor system further comprises other components including tubes, glass media bottles, flow probes, pressure sensors and test software used to obtain the hydrodynamic data during the flow and pressure testing phase.

In one embodiment, the bioreactor may be a rotating bioreactor such as a tubespin bioreactor. Such tube can be placed in a rotisserie for rotisserie culture.

In one embodiment, culturing the cells in the bioreactor system comprises seeding the cells on a bio-scaffold, placing the bio-scaffold in a bioreactor or in a chamber of the bioreactor, and culturing the cells in the culture medium under conditions that augment the number of exosomes released into the culture medium.

In a preferred embodiment, the bio-scaffold comprises polymer materials that may be biocompatible and biodegradable. Such polymer materials include, but are not limited to, PSIS, PGA, polylactic acid (PLA), poly(lactic-co-glycolic) acid (PLGA), PLLA, and PEG. In specific embodiments, the bio-scaffold is made of co-polymers selected from, PGA, polylactic acid (PLA), poly(lactic-co-glycolic) acid (PLGA), PLLA, and PEG. Preferably, the bio-scaffold comprises PGA-PLLA.

In some embodiments, cells seeded on the bio-scaffold in a bioreactor are cultured to confluency (e.g., 60%-99% or 75-95% confluency, such as about 75%, 80%, 85%, 90% or 95%) in culture medium before collecting the conditioned medium fractions from the bioreactor for isolating exosomes from the medium.

In one embodiment, the method comprises seeding the cells on the bio-scaffold at a concentration of at least about $1\times10^5$ cells/mL, $2\times10^5$ cells/mL, $5\times10^5$ cells/mL, or $1\times10^6$ cells/mL.

In one embodiment, the cells used to produce exosomes can be cultured under culture conditions including, for example, static and dynamic culturing, which may be selected from, for example, any one or combinations below:
1) rotisserie culture for N days, N≥1, preferable, N≥7 or 8;
2) no flow culture for X days, X≥1, preferably, X≥7, more preferably, X≥14; and
3) flow culture for Y days, Y≥1, preferably, Y≥7, more preferably, Y≥14, wherein the flow may be selected from high flow (high OSI), the physiological flow (physiological OSI) and low flow (low OSI); and the flow culture may include, for example, continuous flow, oscillatory flow and pulsatile flow culture.

In one embodiment, the pulsatile and/or oscillatory flow pattern is induced by the combination of a cyclic flexure (e.g., 0.5 Hz, 1 Hz, 1.5 Hz, 2 Hz, and any value in between) and steady flow (flex-flow) that induces shear stress, for example, of 2-10 dynes/cm$^2$, 2-9 dynes/cm$^2$, 3-9 dynes/cm$^2$, 2-8 dynes/cm$^2$, 3-8 dynes/cm$^2$, 2-7 dynes/cm$^2$, 3-7 dynes/cm$^2$, 2-6 dynes/cm$^2$, 3-6 dynes/cm$^2$, 2-5 dynes/cm$^2$, 3-5 dynes/cm$^2$, 2-4 dynes/cm$^2$, or 4-5 dynes/cm$^2$.

In one embodiment, the OSI ranges from about 0.05 to about 0.5, from about 0.1 to about 0.5, from about 0.1 to about 0.45, from about 0.1 to about 0.4, from about 0.1 to about 0.38, from about 0.1 to about 0.35, from about 0.1 to about 0.3, from about 0.15 to about 0.35, from about 0.18 to about 0.3, from about 0.2 to about 0.28, or from about 0.2 to about 0.25. In specific embodiments, the OSI is 0.1, 0.11, 0.12, 0.13, 0.14, 0.15, 0.16, 0.17, 0.18, 0.119, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, or 0.4.

In some embodiments, the conditioned medium fractions from the bioreactor may also be collected any time/day under the culture condition above for isolating exosomes. In specific embodiments, the conditioned media from the cells cultured in medium may be collected every 8-100 hours, every 12-72 hours, every 12-60 hours, every 12-48 hours, or every 24-48 hours.

In one embodiment, isolating exosomes from the culture medium comprises filtration and ultracentrifugation of the pooled fractions to obtain an exosome-containing pellet and resuspending the exosome-containing pellet in a buffer, e.g., PBS or saline. In some embodiments, filtration may comprise a step of passing the pooled fractions through a filter, such as a 0.2 μm filter. In a further embodiment, isolating comprises a centrifugation step, for example, prior to filtration to remove any cell debris.

In some embodiments, each medium fraction comprises at least $1\times10^n$ exosomes (n≥6). In one embodiment, each medium fraction may also comprise about $1\times10^9$ to about $1 \times 10^{15}$, about $1 \times 10^{10}$ to about $1 \times 10^{14}$, about $1 \times 10^{11}$ to about $1 \times 10^{13}$, or about $1 \times 10^{11}$ to about $1 \times 10^{12}$, exosomes. In specific embodiments, at least $1 \times 10^{11}$, $5 \times 10^{11}$, $1 \times 10^{12}$, $5 \times 10^{12}$, $1 \times 10^{13}$, $5 \times 10^{13}$, $1 \times 10^{14}$, $5 \times 10^{14}$, or $1 \times 10^{15}$ exosomes are isolated in the collected media fractions.

In one embodiment, the method may further comprise analyzing isolated exosomes using any method that allows direct or indirect visualization of exosomes and may be in vivo or ex vivo. For example, analysis may include, but not limited to, ex vivo microscopic or cytometric detection and visualization of exosomes bound to a solid substrate, flow cytometry, fluorescent imaging, and the like. The exosomes may be analyzed by flow cytometric expression of the exosome surfaces markers, and/or transmission electron microscopy (TEM).

In one embodiment, the subject invention provides agents for cardiac regeneration that are exogenous CSCs. Eight sub-types of CSCs have been identified with varying potential for use as regenerative therapy agents:

1) Cardiosphere-Derived Cells (CDCs); clusters of cardiac progenitor, endothelial and mesenchymal cells which have shown improvement in ventricular ejection fraction and reduction in heart failure status.

2) Sca-1+ CSCs; reside in various regions of the human heart and although they have been shown to be capable of differentiating into cardiomyoblasts, no clinical trials have been conducted with this cell type.

3) Cardiac Mesoangioblasts; shown to exhibit differentiation into cardiomyocytes in vitro, transplanted cells however showed limited proliferation, migration or paracrine activity.

4) Cardiac Side Population cells; possess stem-like properties but their ability to differentiate into cardiomyocitesis under debate and they are depleted with advancing age, they are considered unlikely candidates for clinical studies.

5) Islet-1+ CSCs; cells committed towards the cardiomyocyte lineage with differentiation capability towards all three cardiovascular lineages, their scarcity in the human heart limits their use in cell replacement therapy.

6) Epicardium-Derived Progenitor cells; quiescent epicardial cells shown to undergo epithelial-to-mesenchymal transition post infarct and to migrate into the infarcted myocardium to participate in cardiac repair.

7) Cardiac Colony-Forming-Unit Fibroblasts; exhibit MSC properties with proliferation and differentiation capacities into endothelial and smooth muscle cells, but not into cardiomyocytes, suggesting limited potential for regenerating cardiac muscle.

8) W8B2+ CSCs; reside in human atrial appendages and can differentiate into cardiovascular lineages, showed low engraftment but powerful paracrine effects with promising potential for cardiac therapy and regeneration.

In one embodiment, stem cells are MSCs or CSCs. In a preferred embodiment, MSCs are BMSCs. In some embodiments, CSCs are selected from CDCs, Sca-1+ CSCs, Cardiac Mesoangioblasts, Cardiac Side Population cells, Islet-1+ CSCs, Epicardium-Derived Progenitor cells, Cardiac Colony-Forming-Unit Fibroblasts, and W8B2+ CSCs.

As with MSCs, due to low engraftment of transplanted CSCs, their cardio-preservative benefits can be attributed to the powerful paracrine effects from the release of their exosomes that activate resident stem cells. Preclinical trials show promising results in terms of reduction of infarct size and restoration of cardiac function. CSCs have shown to be superior in terms of in vivo secretion of cardio reparative factors, with W8B2+ and CDCs evidencing greater paracrine potential when compared to BMSCs.

Importantly, CSC-secreted exosomes contain key cardioprotective proteins, lipids and genetic material that can recapitulate the cardio-reparative effects of CSCs when injected into the infarcted myocardium. When injected in animal hearts, the cell-free conditioned media containing the released CSC shows cardio-reparative effects equivalent to transplanting the cells, with implications on how an exosome-containing IESCE could be applied to treat ischemic cardiomyopathy. Administration of cell-free IESCE therapy can provide cardio-reparative effects by activating the paracrine signaling loop in endogenous resident stem cells, which in turn may act as regenerative effectors in situ. The paracrine repair hypothesis has been supported by the fact that CSC exosomes improved cardiac function in the absence of cell transplantation, with preclinical studies having shown that the injected CSC exosome produced cardiac protection and functional improvement in rodents.

In one embodiment, the subject invention provides a method for treating a degenerative disease, the method comprising administering to a subject in need thereof, the composition of the subject invention that comprises exosomes produced according to the method of the subject invention.

In one embodiment, the subject invention provides a method for treating a degenerative disease, the method comprising administering to a subject in need thereof, a therapeutically effective amount of exosomes of the subject invention. "Therapeutically effective" refers to the amount of pharmaceutically active compounds/molecules/particles, e.g., exosomes, according to the subject invention that will result in a measurable desired medical or clinical benefit to a patient, as compared to the patient's baseline status or to the status of an untreated or placebo-treated (e.g., not treated with the compound/molecule/particle) subject.

In one embodiment, the degenerative disease is selected from: cardiovascular disease, arthritis, Friedreich ataxia, Huntington's disease, Kennedy's disease, Marfan syndrome, multiple sclerosis, motor neurone disease (MND), muscular dystrophy, myasthenia gravis, Parkinson's disease, and Alzheimer's disease. Preferably, the degenerative disease is a cardiovascular disease.

In one embodiment, the subject invention provides a method for treating a cardiovascular disease, the method comprising administering to a subject in need thereof, the composition of the subject invention that comprises exosomes produced according to the method of the subject invention.

In one embodiment, the subject invention provides a method for treating a cardiovascular disease, the method comprising administering to a subject in need thereof, a therapeutically effective amount of exosomes of the subject invention.

The term "cardiovascular disease" as used herein refers to any disease or disorder affecting the cardiovascular system, including the heart and blood vessels. A vascular disease or disorder includes any disease or disorder characterized by vascular dysfunction. Particularly preferred cardiovascular diseases are selected from the group consisting of atherosclerosis, a coronary heart disease, an acute coronary symptom (preferably unstable angina pectoris or acute myocardial infarction), stable angina pectoris, stroke (preferably ischemic stroke), ischemic cardiomyopathy, pulmonary hypertension, septic cardiomyopathy, inflammation or autoimmune disease associated artheriosclerosis or restenosis.

In a specific embodiment, the cardiovascular disease is selected from myocardial infarction, ischemic cardiomyopathy, stroke, pulmonary hypertension, coronary heart disease, acute coronary syndromes (ACS), heart valve disease and septic cardiomyopathy.

The term "subject" or "patient," as used herein, refers to an organism, including mammals such as primates. Mammalian species that can benefit from the disclosed methods of treatment include, but are not limited to, apes, chimpanzees, orangutans, humans, and monkeys; domesticated animals such as dogs and cats; livestock such as horses, cattle, pigs, sheep, goats, and chickens; and other animals such as mice, rats, guinea pigs, and hamsters. Preferably, the subject is a human.

The terms "treatment" or any grammatical variation thereof (e.g., treat, treating, etc.), as used herein, includes but is not limited to, the application or administration to a subject (or application or administration to a cell or tissue of a subject) with the purpose of delaying, slowing, stabilizing, curing, healing, alleviating, relieving, altering, remedying, less worsening, ameliorating, improving, or affecting a disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The compositions of the present invention can be administered to the subject being treated by standard routes, including the local, oral, ophthalmic, nasal, topical, transdermal, intra-articular, parenteral (e.g., intravenous, intraarterial, intraperitoneal, intrathecal, intraventricular, intradermal, intracavity, subcutaneous or intramuscular), intracranial, intracerebral, intraspinal, intrauterine, or rectal route. Depending on the condition being treated, one route may be preferred over others, which can be determined by those skilled in the art. Preferably, the composition is administered by injection (e.g., IV injection), gradual infusion over time or implantation.

In a preferred embodiment, the composition of the subject invention or IESCE can be injected onto adversely affected regions via intra-cardiac injections. Multiple injection sites, e.g., 2, 3, 4, or 5 injection sites may be selected for such injection.

In certain embodiments, stem cells such as MSCs and CSCs from which the exosomes are derived can be autologous, allogeneic or xenogeneic. As used herein, the term "autologous" means that the donor of the stem cells such as MSCs and CSCs and the recipient of the exosome (or isolated exosome population) derived from said stem cells such as MSCs and CSCs are the same subject. The term "allogeneic" means that the donor of the stem cells such as MSCs and CSCs and the recipient of the exosome (or isolated exosome population) derived from said stem cells such as MSCs and CSCs are different subjects. The term "xenogeneic" means that the donor of the stem cells such as MSCs and CSCs and the recipient of the exosome (or isolated exosome population) derived from said stem cells such as MSCs and CSCs are subjects of different species. In a particular embodiment, the stem cells such as MSCs and CSCs from which the exosomes derived are allogeneic.

In one embodiment, the subject invention provides a method for promoting tissue regeneration and/or repair, the method comprising identifying a damaged tissue in a subject in need of regeneration and/or repair, and administering to the subject the composition of the subject invention that comprises exosomes produced according to the method of the subject invention.

In one embodiment, the subject invention provides a method for promoting tissue regeneration and/or repair, the method comprising identifying a damaged tissue in a subject in need of regeneration and/or repair, and administering to the subject a therapeutically effective amount of exosomes of the subject invention.

In one embodiment, the tissue in need of regeneration and/or repair includes, for example, damaged tissues, necrotic tissues, tissues after surgery, tissues with reduced function, fibrosing tissues, aged tissues, and diseased tissues. Examples of the tissues include live skin tissues and tissues obtained by internal biopsy (surgery) (brain, lung, heart, liver, stomach, small intestine, large intestine, pancreas, kidney, urinary bladder, spleen, uterus, testis, blood, bone, cartilage, fat, skeletal muscle, epithelial tissues etc.).

The method of the subject invention contributes to functional regeneration of the tissue in need of regeneration and maintenance/enhancement of function. In the present invention, examples of tissue in need of regeneration include, but are not limited to, tissues damaged by various pathological conditions due to ischemic/hypoperfusive/hypoxic conditions, trauma, burns, inflammation, autoimmunity, gene abnormalities, and the like. With use of the above tissue regeneration-promoting agents and compositions, treatments for inducing functional tissue regeneration becomes possible not only in cutaneous diseases such as intractable cutaneous ulcers, skin wounds, bullosis, and alopecia, but also in tissues in need of regeneration such as cerebral infarction, myocardial infarction, bone fracture, pulmonary infarction, gastric ulcers, and enteritis.

In one embodiment, the compositions can be administered to a subject by methods including, but not limited to, (i) administration through oral pathways, which administration includes administration in capsule, tablet, granule, spray, syrup, or other such forms; (ii) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, and the like; as well as (iii) administration topically, or as deemed appropriate by those of skill in the art for bringing the compound into contact with living tissue; and (iv) administration via controlled released formulations, depot formulations, and infusion pump delivery.

For example, for parenteral administration in an aqueous solution, the solution should be suitably buffered and the liquid diluent first rendered isotonic with sufficient saline or glucose. Sterile aqueous media that can be employed will be known to those of skill in the art in light of the present disclosure. One may also use nasal solutions or sprays, aerosols or inhalants in the present disclosure. Nasal solutions may be aqueous solutions designed to be administered to the nasal passages in drops or sprays.

Oral formulations can include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. A person of ordinary skill in the art would be familiar with well-known techniques for preparation of oral formulations.

The subject invention contemplates the use of compositions that are sterile solutions for intravascular injection or for application by any other route. A person of ordinary skill in the art would be familiar with techniques for generating sterile solutions for injection or application by any other route. Sterile injectable solutions are prepared by incorporating the active agents in the required amount in the appropriate solvent with various of the other ingredients familiar to a person of skill in the art.

For the treatment of disease, the appropriate dosage of a therapeutic composition will depend on the type of disease to be treated, as defined above, the severity and course of the disease, the patient's clinical history and response to the agent, and the discretion of the attending physician. The composition of the subject invention is suitably administered to the patient at one time or over a series of treatments.

Administration can be carried out using therapeutically effective amounts of the agents described herein for periods of time effective according to the subject invention. The effective amount may be determined by one of ordinary skill in the art and includes exemplary dosage amounts for a subject of from about 0.005 to about 500 mg/kg of body weight of active compound per day, which may be administered in a single dose or in the form of individual divided doses, such as from 1 to 4 times per day.

Alternatively, the dosage amount may be from about 0.01 to about 400 mg/kg of body weight of active agent per day, from about 0.05 to about 300 mg/kg of body weight of active agent per day, from about 0.1 to about 200 mg/kg of body weight of active agent per day, from about 0.1 to about 150 mg/kg of body weight of active agent per day, from about 0.2 to about 100 mg/kg of body weight of active agent per day, from about 0.5 to about 100 mg/kg of body weight of active agent per day, from about 0.5 to 50 mg/kg of body weight of active agent per day, from about 1 to about 50 mg/kg of body weight of active agent per day, from about 1 to about 25 mg/kg of body weight of active agent per day, or from about 1 to about 10 mg/kg of body weight of active agent per day.

In specific embodiments, the composition of the subject invention may be administered at least once a day, twice a day, or three times a day for consecutive days, e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

In one embodiment, the subject invention provides a method for producing a tissue-engineered valvular construct (TEVC) for the treatment of critical congenital heart valve disease. The general approach to dynamically culture tissue engineered valves begins with seeding of the cells on a scaffold of choice and placing them in a bioreactor that simulates the mechanical conditions to support valvular tissue formation and a phenotype of interest.

In one embodiment, the subject invention provides a method for promoting MSCs (e.g., hBM-MSCs) differentiation toward a-SMA and CD31 valvular phenotypes, the method comprising seeding MSCs on a bio-scaffold, placing the bio-scaffold in a chamber of a bioreactor, dynamically culturing MSCs in a culture medium under conditions according to the subject invention, wherein the bioreactor comprises a pulsatile flow pump that provides dynamic flow conditions to the cultured MSCs.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

As used herein, each of n, N, X and Y is intended to include $\geq 1$, $\geq 2$, $\geq 3$, $\geq 4$, $\geq 5$, $\geq 6$, $\geq 7$, $\geq 8$, $\geq 9$, $\geq 10$, $\geq 11$, $\geq 12$, $\geq 13$, $\geq 14$, $\geq 15$, $\geq 16$, $\geq 17$, $\geq 18$, $\geq 19$, $\geq 20$, $\geq 21$, $\geq 22$, $\geq 23$, $\geq 24$, $\geq 25$, $\geq 26$, $\geq 27$, $\geq 28$, $\geq 29$, and $\geq 30$.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

It should be understood that the examples and embodiments described herein are for illustrative purposes only and that various modifications or changes in light thereof will be suggested to persons skilled in the art and are to be included within the spirit and purview of this application.

EXAMPLES

Materials and Methods

Human Mesenchymal Stem Cells Culture

Static (no flow) vs Dynamic (Flex-stretch-flow Bioreactor). Human mesenchymal stem cells (MSCs; RoosterBio, Frederick, MD) were cultured in cell culture media (RoosterBasal™-MSC, RoosterBio, Frederick, MD) and supplement (RoosterBooster™-MSC-XF, RoosterBio, Frederick, MD).

Static (Rotisserie) vs Dynamic (Torpedo Bioreactor). Human mesenchymal stem cells (MSCs; RoosterBio, Frederick, MD) were cultured in cell culture media (RoosterBasal™-MSC, RoosterBio, Frederick, MD) and supplement (RoosterBooster™-MSC-XF, RoosterBio, Frederick, MD) with 1% penicillin and streptomyocin (Thermo Scientific™ HyClone™ Fisher Scientific) until confluency.

Scaffold Preparation and Cell Seeding

Static (no flow) vs Dynamic (Flex-stretch-flow Bioreactor). An equal ratio of poly-glycolic acid (PGA) and poly-L-lactic acid (PLLA) non-woven polymer felt (PGA-PLLA; Biofelt, Biomedical Structures, Warwick, RI) and porcine small intestine submucosa (PSIS; Cormatrix Inc., Roswell, GA) scaffolds were seeded with MSCs (7 million cells per scaffold). Tissue culture medium used for culture were composed of Dulbecco's modified Eagle's medium (DMEM; Corning, Fisher Scientific, Pittsburgh, PA), 10% fetal bovine serum (Corning, Fisher Scientific, Pittsburgh, PA), 1% penicillin and streptomycin, 2 ng/ml basic fibroblast growth factor (bFGF; Corning™, Fisher Scientific) and 82 µg/ml ascorbic acid 2 phosphate (AA2P; Sigma-Aldrich, Dorset, UK). After the MSCs were seeded on the scaffolds, the scaffolds were subjected to 8 days of rotisserie culture using a rotisserie (Labquake™ Rotisserie Hybridization Rotators, Thermo Scientific, USA) at 8 rpm in the incubator with controlled cell culture conditions (37° C., 5% CO2) for 8 days without media change. At the end of day 8, scaffolds were split into two groups: 14 days of no flow condition (static) and 14 days of flow condition (dynamic, bioreactor). Time-Averaged fluid-induced mechanical shear stress of the flow environment was at 3.1 dynes/cm$^2$, with the magnitude of flow oscillations, given by the oscillatory shear index (OSI) was an OSI=0.20.

At the end of day 22, tissue culture medium from both static and dynamic groups were collected. Medium was centrifuged at 3000×g for 15 minutes. Supernatant was transferred to a sterile vessel and adequate amount of ExoQuick-TC precipitation solution (System Biosciences, Palo Alto, CA). The mixture was stored overnight at 4° C. Afterwards, the mixture was centrifuged at 1500×g for 30 minutes. Exosomes pellet were resuspended and collected.

Static (Rotisserie) vs Dynamic (Torpedo Bioreactor). Porcine small intestine submucosa (PSIS; Cormatrix Inc., Roswell, GA) scaffolds were seeded with MSCs in rotisserie culture for 8 days (7 million cells per PSIS valve). Tissue culture medium used for culture were composed of Dulbecco's modified Eagle's medium (DMEM; Corning, Fisher Scientific, Pittsburgh, PA), 10% fetal bovine serum (Corning, Fisher Scientific, Pittsburgh, PA), 1% penicillin and streptomycin, 2 ng/ml basic fibroblast growth factor (bFGF; Corning™, Fisher Scientific) and 82 µg/ml ascorbic acid 2 phosphate (AA2P; Sigma-Aldrich, Dorset, UK). After 8 days of rotisserie culture, one of the groups continued another 14 days of rotisserie (static) and another group proceeded to the torpedo bioreactor conditioning environment (dynamic) for 14 days.

At the end of day 22, tissue culture medium from both static and dynamic groups were collected. Medium was centrifuged at 3000×g for 15 minutes. Supernatant was transferred to a sterile vessel and adequate amount of ExoQuick-TC precipitation solution (System Biosciences, Palo Alto, CA). The mixture was stored overnight at 4° C. Afterwards, the mixture was centrifuged at 1500×g for 30 minutes. Supernatant was saved for non-exosomal analysis. Exosomes pellet were resuspended and collected.

Tissue Engineering

After the hBM-MSCs were seeded on the scaffolds, the specimens were subjected to 8 days of rotisserie culture; next, they were split into two groups: (1) no flow (static controls) and (2) physiological oscillatory flow (bioreactor group). The cell-seeded specimens in the no flow group were immersed in media within a 6-well plate and left within in a tissue culture incubator for an additional 14 days without media change. Meanwhile for the oscillatory flow group, the cell-seeded specimens were sutured on both ends to metallic springs and inserted onto stationary rods within a U-shaped bioreactor device. The bioreactors were then connected to a pneumatic piston pulsatile flow pump, with a pump head module (ViVitro Labs Inc., Victoria, BC, Canada) that housed the tubing to transport media to the specimens housed within the bioreactors (one bioreactor chamber contained another scaffold material that was conditioned identically, but not connected to the present study). Physiologically relevant fluid-induced wall shear stresses (WSS) of 3-9 dynes/cm2 can be conducive to proper cell conditioning. Similarly, fluid oscillations, measured with oscillatory shear index (OSI), between 0.18 and 0.23 can assist in promoting genes that support the valve phenotype. Hence, an aortic flow waveform, which could elicit valve relevant of TAWSS and OSI was applied to the bioreactor for an additional 14 days, beyond the initial 8-days rotisserie culture period. Total culture time of the engineered tissue constructs in both the static and bioreactor time was therefore 22 days, which consisted of 8 days rotisserie culture followed by either an additional 14 days static or 14 days pulsatile flow culture.

Immunofluorescence

Once the experiment was complete, the scaffolds were prepared for immunofluorescence assessment similar. In brief, the scaffolds were fixed in formalin (10% v/v) for 24 h followed by embedding in a slow freeze process in optimal cutting temperature (OCT). The embedded samples were then placed in −80° C. overnight and then sliced (16 µm of thickness) and placed on glass slides (TruBond 380, Newcomer Supply, Middleton, "Wisconsin") and left to dry at room temperature to allow for immunofluorescence staining. The slides were stained with primary antibodies for valvular components, including endothelial and interstitial cells; CD31 was used as an endothelial cell marker (Invitrogen, REF: PA5-14372), and alpha smooth muscle actin (a-SMA) was used as an interstitial cell marker (Invitrogen, REF: 14-9760-82), separately. Donkey antirabbit (Abcam, ab150073) and donkey antimouse (Abcam, ab150108) were used as secondary antibodies, respectively, for CD31 and a-SMA. Immunofluorescence images were captured with confocal microscopy (Nikon Eclipse Ti, Minato, Tokyo, Japan).

All samples from the static control and oscillatory flow groups were stained for CD 31 and a-SMA immunostaining at the same time. The signal intensities in all groups were normalized relative to the average intensity of the static samples.

Protein Quantification

Figure 4A:
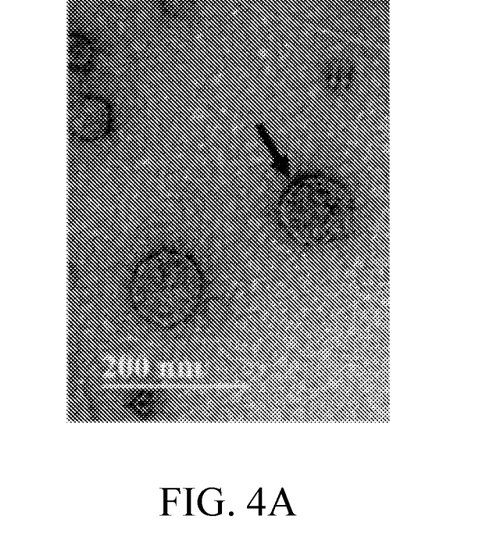
FIGS. 4A-4B. Bulk assessment of IESCE: (4A) Transmission electron microscopy (TEM) of exosomes isolated from BMSC-seeded scaffolds (both PSIS and PGA/PLLA) after pulsatile flow conditioning in our bioreactor for 2 weeks, after an initial 8 days of rotisserie culture. The arrow points to an extracellular body that was positively labeled with the CD9 antibody which confirms that it is an exosomal component. (4B) A minimum of 2.8 times increase in total protein was present in exosomes constituting IESCE after bioreactor-based, physiologically-relevant pulsatile flow conditioning for 2 weeks, following 8 days of rotisserie culture seeding, as compared to static controls. PSIS: porcine small intestinal submucosa bioscaffold. PGA/PLLA: poly-glycolic acid/poly-L-lactic acid synthetic scaffold.

Conditioned media was collected from static, 8-days rotisserie, and oscillatory flow groups and centrifuged at 3,000×g for 15 min to remove cell debris. An appropriate volume of ExoQuick-TC solution (System Biosciences, Palo Alto, CA) was added to each group to precipitate the exosomes that were secreted by hBM-MSCs. The media/ExoQuick-TC mixture was refrigerated overnight (~16 h) at 4° C. and then centrifuged at 1,500×g for 30 min. The supernatant was removed, and the residual of ExoQuick-TC precipitation solution was aspirated after the centrifugation at 1,500×g for 5 min. Exosome pellets were resuspended in 250 µl phosphatebuffered saline (PBS) and filtered with 0.2-µm syringe filters (Thermo Scientific™ Nalgene™, Fisher Scientific, Hampton, NH) (FIG. 4a).

To examine the quantity of protein, radioimmunoprecipitation assay (RIPA) buffer (Fisher Scientific, Pittsburgh, PA) was added to lyse the samples at, e.g., 1:1 ratio. Sample lysates were sonicate for 30 seconds and shake in ice for 15 minutes. Afterwards, the lysates were centrifuged at 14000×g for 15 minutes. Supernatant was then saved. Protein quantification was done by using DC™ Protein Assay Kit II (Bio-Rad Laboratories, Inc., Hercules, CA). Prepare adequate amount of reagent A' (reagent A+reagent S) and standard. Add 5 µL of standards and samples to 96-well plate. Add 25 µL of reagent A' and 200 µL of reagent B to each well. After incubating at room temperature for 15 minutes, absorbances were read at 750 nm by spectrophotometer (Synergy HT, BioTek Instruments Inc., Winooski, VT).

Mass Spectrometry Analysis

In order to prepare the samples for mass spectrometry detection, In-Solution Tryptic Digestion and Guanidination Kit (Fisher Scientific, Pittsburgh, PA) was used. 15 µL of Digestion Buffer and 1.5 uL of Reducing Buffer were prepared and added to the microcentrifuge tubes, which is followed by adding ≤10.5 uL of lysate containing 0.025-10 µg of protein (based in the results from protein quantification) and adjusting the final volume to 27 uL with ultrapure water. Samples were incubated at 95° C. for 5 minutes. Alkylation Buffer was prepared and 3 µL of the buffer was added to the samples. Samples were incubated in the dark at room temperature for 20 minutes. Activated Trypsin was prepared and added (1 uL) to the samples. Samples were incubated at 37° C. for 3 hours. Additional 1 µL of Activated Trypsin was added to the sample and incubate at 37° C. for 2 hours. Finally, 3 µL of formic acid (Optima™ LC/MS Grade, Fisher Chemical™, Pittsburgh, PA) was added to stop the reaction.

Liquid Chromatography-Tandem Mass Spectrometry (LC-MSMS) Analysis

Liquid chromatography-tandem mass spectrometry (LC-MSMS) analysis was conducted on a Bruker tims-TOF UHR MS (Bruker Scientific. Billerica, MA) instrument operated in positive (+) ion mode in the mass range from 300 to 1900. Chromatography separation was conducted utilizing a 46-min-long LC method. Moreover, the in-solution digested extracts were diluted and stored in silanized glass inserts placed inside a sampling vial, which were then loaded onto a high-performance liquid chromatography (HPLC) autosampler (Shimadzu Prominence, Nakagyo-ku, Japan). Thereafter, a 20 µl aliquot was injected into the HPLC for separation prior to mass spectrometry (MS) analysis. After data acquisition, the obtained raw mass spectrometry data was processed using Peaks Studio X± (Bioinformatics Solution Inc., Waterloo, ON, Canada) for protein identification and peptide sequencing.

Example 1—BMSC-Seeded Bioscaffolds

Figure 1:
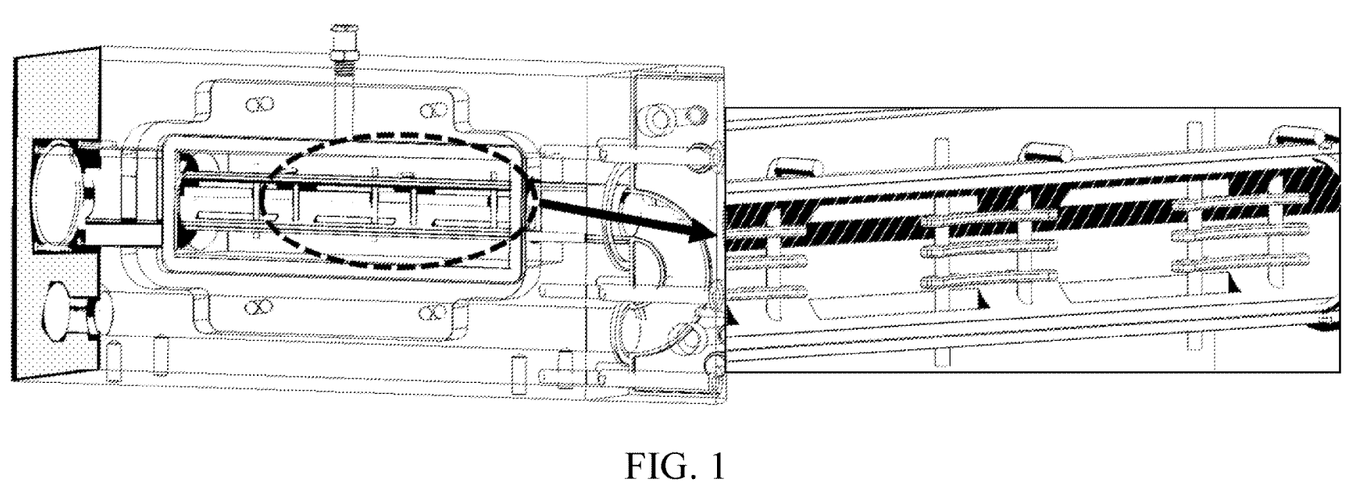
FIG. 1. Customized bioreactor that allows for the connection to a pulsatile flow pump that will deliver aorta-relevant fluid oscillations that lead to secreted cardiovascular factor accumulation in the conditioned media. The three tissue strips (encircled in figure) when seeded with human BMSCs, secrete extracellular matrix (ECM) that exhibits a strong cardiovascular phenotype after a 22-day culture period. Isolation of the released secretory factors into the media, i.e., the IESCE, is of interest.

BMSC-seeded bioscaffolds subjected to physiologically-relevant pulsatile flow in vitro will lead to accumulation of a potent BMSC-derived exosome product in the conditioned media, i.e., the IESCE, which will contain a rich presence of a trophic factor cocktail that will promote cardiac repair and function post-MI. This is because when BMSCS are exposed to fluid-induced oscillatory shear stresses arising from pulsatility (FIG. 1), stem cells will express cardiovascular-relevant genes and release trophic molecular factors into the media, which will aid in regeneration and healing.

Example 2—Modifications to the Bioreactor

The bioreactor can be modified (FIG. 2) to permit the conditioning chamber to house a cylindrical bio-scaffold sleeve. Hence, a substantially higher number of stem cells can be seeded on to the much larger sleeve surface area (about 1 million cells/cm$^2$ on the side exposed to flow), and then oscillatory flow-conditioned, to further augment the number of exosomes released into the culture media. To evaluate the IESCE efficacy, three treatments are investigated-(i) exosomes derived from statically cultured, adult, human BMSCs (ii) IESCE derived from physiologically-relevant, oscillatory flow-conditioned adult, human BMSCs and (iii) exosomes derived from statically cultured, adult, human CSCs.

The flow-stretch-flex (FSF) bioreactor geometry primarily comprises a U-shaped housing with a constant internal diameter of 13 mm. Each side of the cell-seeded scaffold specimens was identified as either the proximal or distal side relative to its physical distance to the centerline axis of the bioreactor.

Specific components of the bioreactor system include a separable and insertable cylindrical specimen holder, U-shaped bioreactor chambers that housed the hBMMSC-seeded scaffolds, and flow that was facilitated by a programmable pulsatile pump system (ViVitro Labs Inc., Victoria, BC, Canada). Scaffolds can be placed in each bioreactor chamber in a parallel configuration to the flow direction and fully immersed in the media solution. Other components include tubes, glass media bottles, flow probes, pressure sensors and test software used to obtain the hydrodynamic data during the flow and pressure testing phase.

Example 3—Evaluating the Benefits of IESCE in a Non-Human Primates

Primate (*Hamadryas baboon*) study (n=4; age ~ 8 years old) of MI. Local ischemia is created within the heart muscle during surgery by temporarily occluding the main segments of the coronary arteries, until MI occurs, which will be evident by visible changes in heart contraction and by electrocardiogram recordings. The changes can be captured spatially by real-time echocardiography analysis both before and after MI-induction. Next, IESCE is delivered to the adversely affected regions via intra-cardiac injections. The animals will be monitored longitudinally for 12 months using echocardiography for evaluation of heart function followed by terminal histological and immune-histochemical analysis. For in vivo assessment, IESCE will be derived identically as in Example 2 except that the source of BMSCs is allogeneic, i.e., from adult baboons (8 years old). This approach ensures that no bioactive molecule is left behind, i.e. a cocktail of factors will be present within the IESCE, so that the complex interaction by individual factors as well as between molecules lead to robust micro-to-macro level neovascularization, reduction of scar tissues and resuscitation of cardiomyocytes through paracrine mediated signaling from the stem cell-associated trophic factors. Moreover, IESCE are void of any living component, thereby making the technology practical to maintain, regulate, keep sterile, package and deliver to a clinical setting. Thus, IESCE revolutionize the treatment of MI. Broadly, IESCE serve as a therapeutic to promote repair and regeneration of any cardiovascular tissue which includes diseases of the heart, blood vessels and the heart valves.

Figure 3A:
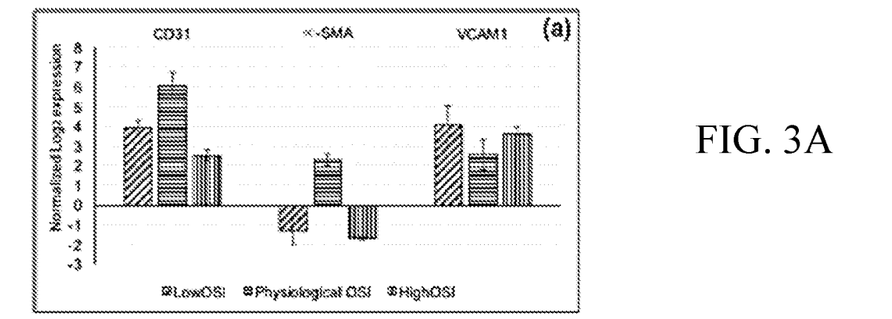
Figure 3B:
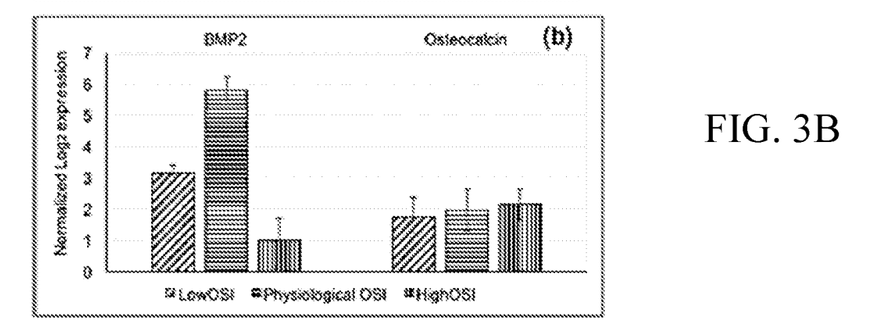
Figure 3C:
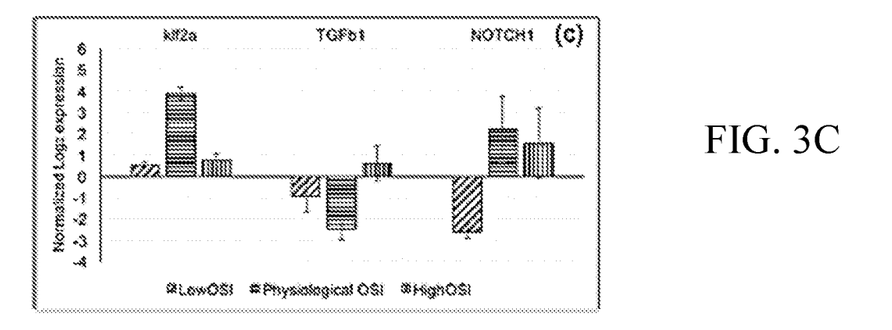

Example 4—Valve Phenotype Obtained by Physiologically-Relevant Pulsatile Flow Condition Valve phenotype can be directly obtained by applying a physiologically-relevant pulsatile flow condition which facilitates oscillation of the culture media onto BMSCs. Fluid oscillations can be quantified by the oscillatory shear index (OSI) with a range of $0 \leq OSI \leq 0.5$, with zero depicting one-directional flow and 0.5 describing maximum oscillatory flow. A physiological OSI range for stimulating BMSCs was $0.18 \leq OSI \leq 0.23$, which yielded maximum phenotypic benefits (FIG. 3A-3C).

Example 5—Bulk Assessment of IESCE

Figure 4B:
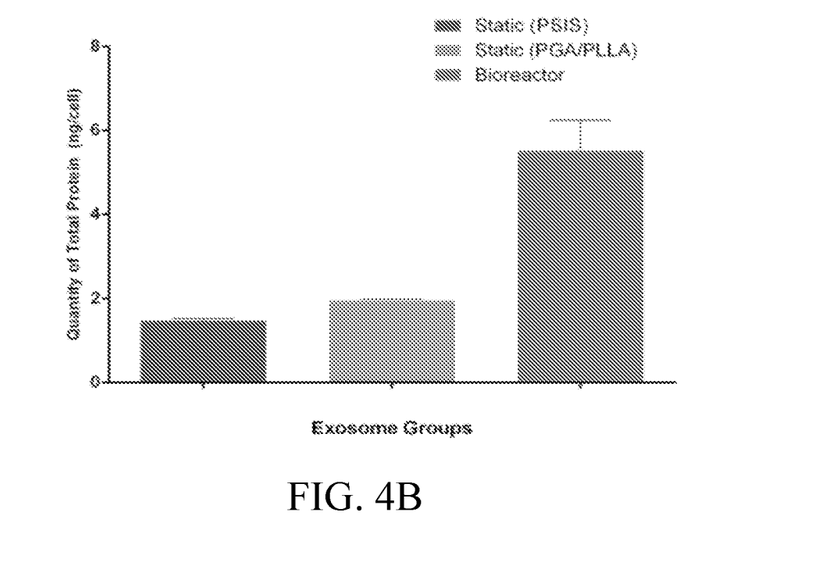

Bulk biochemical assessment of isolated exosomes which forms the primary basis for the IESCE, i.e., which were taken from BMSCs conditioned in the bioreactor exhibited considerably higher total protein relative to static controls (FIG. 4A-4B).

Figure 5A:
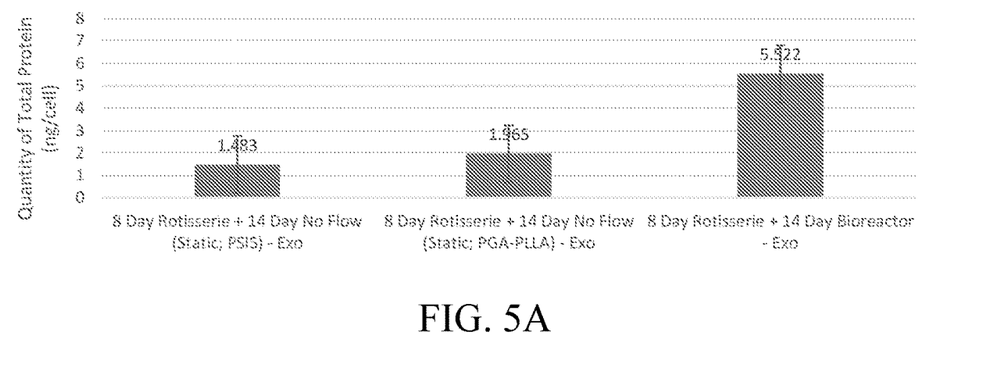
FIGS. 5A-5B. Protein quantification. 5A) total protein secreted by the exosomes isolated from the bioreactor conditioning for 2 weeks, following 8 days of rotisserie culture seeding, as compared to static controls. 5B) mass spectrometry measurements show that fibronectin is significantly lower ($p<0.05$) in the bioreactor culture (dynamic: flex-stretch-flow bioreactor) compared to static environments (no flow).

The total protein in exosomes produced by stem cells was quantified where stem cells were cultured under the following conditions: 1) 22 Day Static (PSIS): 8-day rotisserie and 14-day no flow; 2) 22 Day Static (PSIS-PLLA): 8-day rotisserie and 14-day no flow; and 3) 8-Day Rotisserie and 14-Day Bioreactor. The result shows that total proteins in exosomes produced by stem cells were significantly higher (p<0.05) after bioreactor conditioning (flex-stretch-flow Bioreactor) compared to static culture (FIG. 5A). The quantity of total protein was shown in Table 1.

TABLE 1

| Quantity of Total Protein (ng/cell) | |
|---|---|
| Experimental Groups | Means ± SEM |
| 22 Day Static (PSIS) – Exo | 1.483 ± 0.043 |
| 22 Day Static (PSIS-PLLA) – Exo | 1.965 ± 0.034 |
| 8 Day Rotisserie + 14 Day Bioreactor – Exo | 5.522 ± 2.077 |

Fibronectin is an important component of extracellular matrix and blood plasma and it is also a ligand for integrin adhesion receptor. Fibronectin has various functions including embryonic development, wound healing, fibrosis, and immune and inflammatory responses. It is increased during postnatal development and decreased with progression to adulthood. Fibronectin is considered a good source in order to help form a cell supporting matrix for connective tissues and tissue repair after the injury. However, fibronectin is overexpressed after heart injury such as myocardial infarction and atherosclerosis. The overexpressed fibronectin may further contribute to cardiac fibrosis.

Figure 5B:
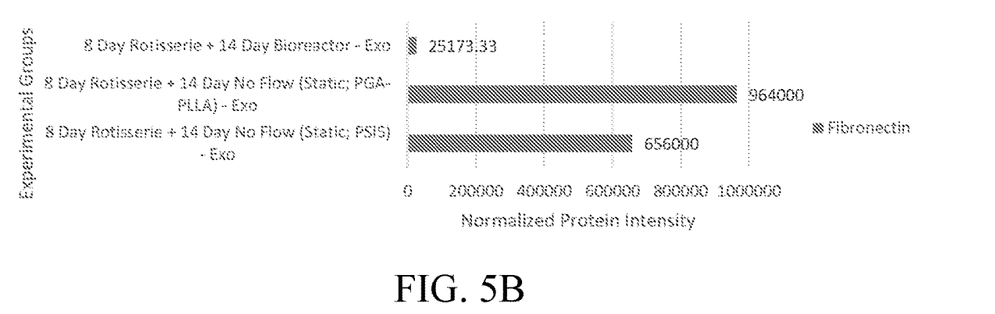

The results show that fibronectin, the protein detrimental to cardiac tissue, was significantly lower (p<0.05) in the bioreactor culture (dynamic: flex-stretch-flow bioreactor) compared to static environments (no flow) (FIG. 5B). The raw protein intensities were measured to be 6293 in the IESCE group, compared to a value of 241000 under static (normal) culture for the same total culture period for both groups. Thus, the IESCE group provides a 97.4% reduction of Fibronectin. Therefore, exosomes secreted under the bioreactor condition advantageously produce a lower level of fibronectin.

Figure 6:
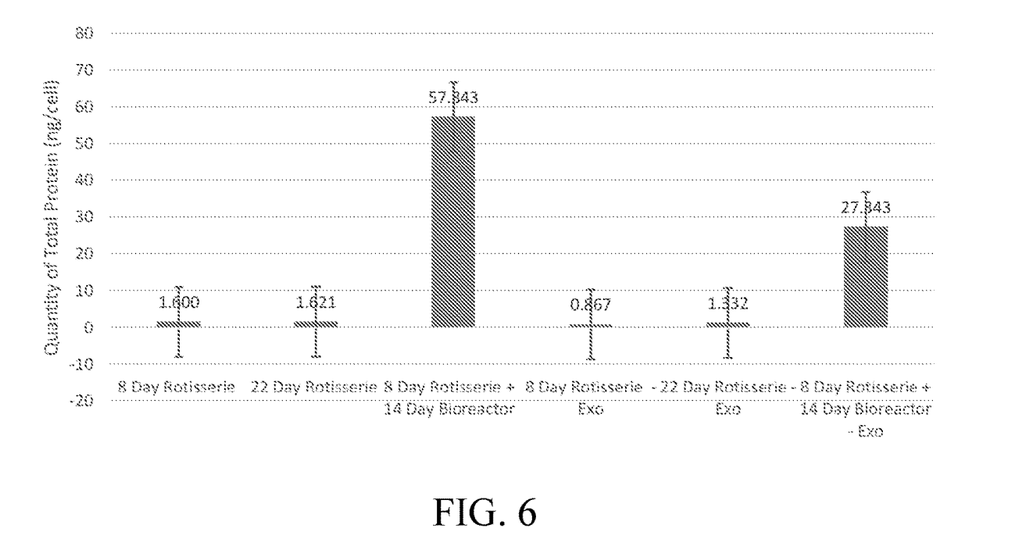
FIG. 6. the amount of total protein secreted by the exosomes and non-exosomal products isolated from the bioreactor media as compared to static controls.

Moreover, the amount of total proteins secreted by the exosomes and non-exosomal products were quantified. The results show that total proteins in exosomes produced by stem cells and non-exosomal products isolated from culture media were significantly higher (p<0.05) after bioreactor conditioning (Torpedo bioreactor) compared to static culture (Rotisserie) (FIG. 6). The quantity of total protein and non-exosomal products was shown in Table 2.

TABLE 2

| Quantity of Total Protein (ng/cell) | |
|---|---|
| Experimental Groups | Means ± SEM |
| 8 Day Rotisserie | 1.600 ± 0.018 |
| 22 Day Rotisserie | 1.621 ± 0.021 |
| 8 Day Rotisserie + 14 Day Bioreactor | 57.343 ± 0.042 |
| 8 Day Rotisserie – Exo | 0.867 ± 0.027 |
| 22 Day Rotisserie – Exo | 1.332 ± 0.083 |
| 8 Day Rotisserie + 14 Day Bioreactor – Exo | 27.343 ± 0.025 |

Figure 7:
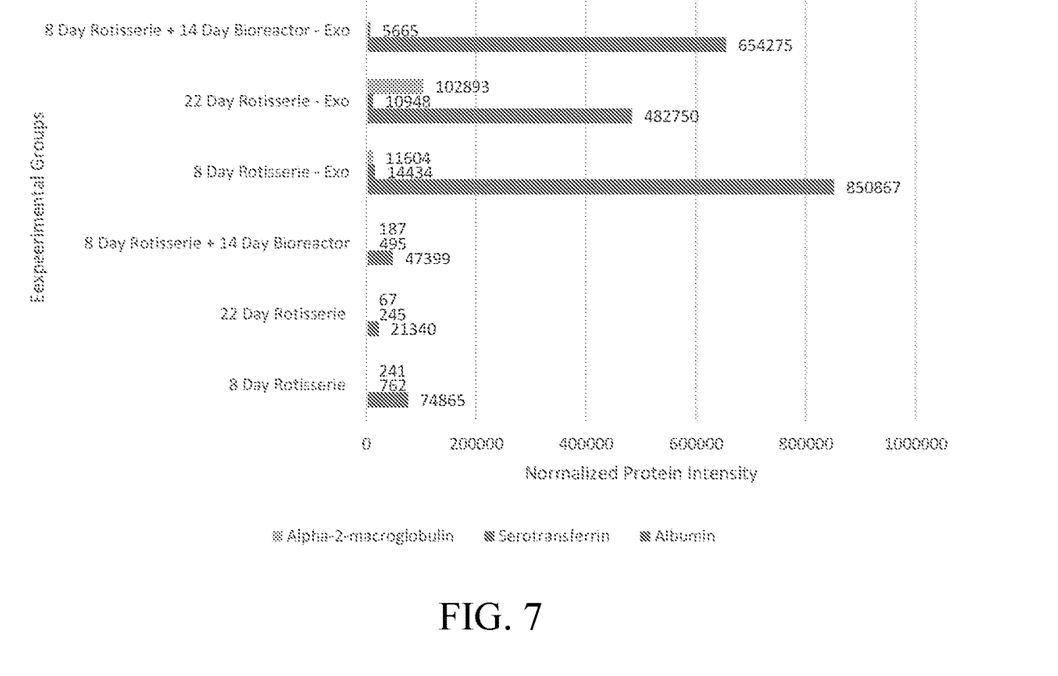
FIG. 7. mass spectrometry measurements of serum album, serotransferrin, and alpha-2-macroglobulin in the bioreactor culture as compared to static controls.

Even though there was higher total proteins in the non-exosome component of the spent media from the bioreactor group, the specific types of cardiac relevant proteins such as serum albumin, serotransferrin, and alpha-2-macroglobulin were negligible in the non-exosome component compared to the exosome component (FIG. 7). This suggests that the proteins in the non-exosomal components of the spent media are largely proteins being added to the media to facilitate cell culture (e.g., fetal bovine serum (FBS)) rather that proteins secreted by the stem cells.

Serum album was the most prevalent protein found in all exosomal groups compared to non-exosomal groups. Serum albumin has functions of maintaining oncotic pressure and microvascular integrity, regulating metabolic and vascular functions, antioxidant activities, and anticoagulant effects. Low serum albumin concentration may contribute to adverse cardiovascular events, such as chronic stable coronary artery disease and increase the risk for heart failure in the elderly population.

Serotransferrin was only detected in the exosomal groups. Serotransferrin functions as an iron binding transport protein that transports iron from sites of absorption and heme degradation to those of storage and utilization. It also plays a role in cell proliferation. Lack of transferrin may cause iron deficiency and severe iron deficiency was found to cause left ventricular (LV) dysfunction and overt heart failure. Lower level of serotransferrin was found in patients with rheumatic valvular disease.

Alpha-2-macroglobulin contributes to several adverse health problems. Alpha-2-macroglobulin can induce transcriptional activation of some genes essential for the proliferation and hypertrophy of cells, oncogenesis and atherosclerosis. A cardiac isoform of alpha-2-macroglobulin can activate the expression of muscle-specific genes that are associated with the pressure-overloaded heart and can cause cardiac hypertrophy directly. Even though alpha-2-macroglobulin was detected in two of the exosomal groups (8 Day Rotisserie-Exo and 22 Day Rotisserie-Exo), it was not produced by the bioreactor Compared to the static groups (8-day and 22-day rotisserie), the exosomes in the Bioreactor group had reasonable quantities of albumin, mild amounts of serrotransferin and no presence of alpha-2-macroglobulin. These are important proteins to aid in cardiac repair/regeneration. While they were not present in maximum concentrations in the bioreactor group, the exosomes derived from the stem cells in bioreactor dynamic culture is still preferable due to the minimal presence of fibronectin and the maximum expression of total proteins (FIGS. 5A and 6).

The specific mechanical and chemical environments in the bioreactor of the subject invention can be varied to yield even higher concentrations of cardiac therapeutic proteins particularly when these conditions mimic pathology. For example, hypoxic conditions increase the number of exosomes secreted by stem cells and these exosomes contain molecular cargo of higher quality. Hypoxic conditions can be combined with abnormal dynamic mechanical environments in the bioreactor that mimics blood flow in a cardiovascular disease state.

Example 6—Mechanical Conditioning BMSCs

A physiologically-representative dynamic culture program induces stem to CV cell differentiation. Mechanically conditioned BMSCs can be seeded onto biodegradable porcine ECM (Cormatrix Inc., Roswell, GA) strips for 2 weeks in a bioreactor after 8 days of rotisserie tissue culture. At the end of 22-days of culture, the conditioned media can be evaluated via proteomics, cytokine panel analysis and phenotypically (RT-PCR), specifically for identification of bioactive molecular factors.

Figure 2:
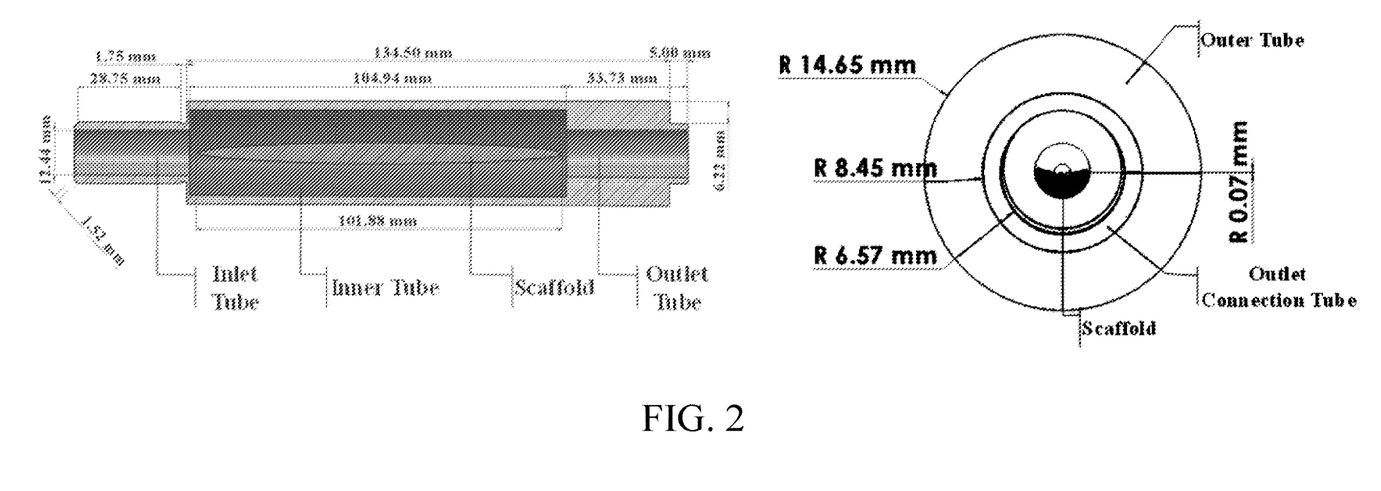

A bioreactor system of FIG. 2 can be modified to accommodate a BMSC-seeded 2-ply-PSIS sheet (about 1 million cells/cm$^2$ on the side exposed to flow; thickness ~ about 100 µm) that is rolled into a tube and is inserted as a sleeve into the upper part of the U-shaped conditioned chamber, which is currently occupied by three scaffold strips. A specific mechanical conditioning protocol can be applied to promote relevant CV phenotypes via a straightforward application of using solely an aortic pulsatile flow waveform. This waveform induces oscillatory flow patterns onto the BMSC-seeded scaffold sleeve, thereby leading to the release of reparative factors for cardiac tissue into the media. The original media can comprise of DMEM supplemented with the following: 10% exosome-free fetal bovine serum, 2% antimycotics/antibiotics, 81 mg/ml ascorbic acid and 2 ng/ml fibroblast growth factor. The conditioned media can be saved for analysis at the end of the 2-week bioreactor pulsatile flow conditioning time frame. This procedure can be repeated with CSCs.

The phenotypic changes to the engineered tissue constructs were assessed after being subjected to oscillatory shear stresses resulting from the aortic flow profile, in comparison to oscillatory patterns in the culture media induced under a combination of steady flow and cyclic flexure, i.e., flex-flow (cyclic flexure of 1 Hz and steady fluid-induced shear stress of 4-5 dynes/cm$^2$). The oscillations were solely fluid induced, without any structural deformation (e.g., cyclic flexure or cyclic stretch) of the specimens.

Figure 8A:
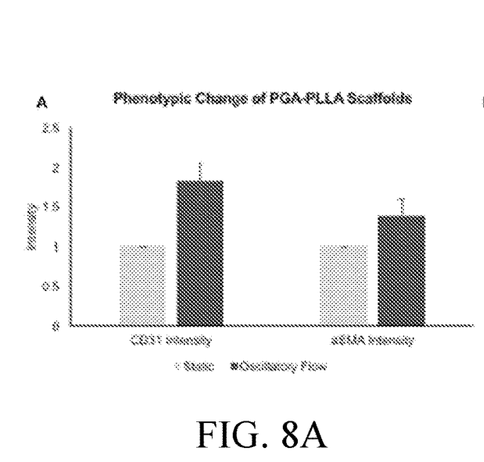
FIGS. 8A-8B. hBM-MSCs differentiation toward a-SMA and CD31 valvular phenotypes and fibronectin protein intensity in collected media. PGA-PLLA scaffolds seeded with hBM-MSCs demonstrating (8A) average intensity values of a-SMA and CD31 in static and oscillatory flow groups. There was a significant difference ($p<0.05$) in both a-SMA and CD31 phenotypes intensities between the groups. In the oscillatory flow group there was an increase in both a-SMA and CD31 compared to the static group (significant, $p<0.05$). (8B) Media was collected and fibronectin intensities were assessed for static, 8-day rotisserie and oscillatory flow groups. The oscillatory flow group was significantly lower ($p<0.05$) than both the static and 8-day rotisserie groups.

Immunofluorescence analysis shows that for a-SMA, the average intensities were found to be 1.0±0.15 and 1.4±0.11 for static and oscillatory flow, respectively (FIG. 8A). For CD31, the average intensities were 1.0±0.18 and 1.8±0.26 for static (n=12) and oscillatory flow (n=10), respectively (FIG. 8A). These immunofluorescence intensity assessment demonstrated that the a-SMA quantification between the groups (i.e., average static and oscillatory flow) were significantly different ($p<0.05$) (FIG. 8A); similarly, the CD31 levels were found to be significantly different ($p<0.05$) (FIG. 8A).

Figure 8B:
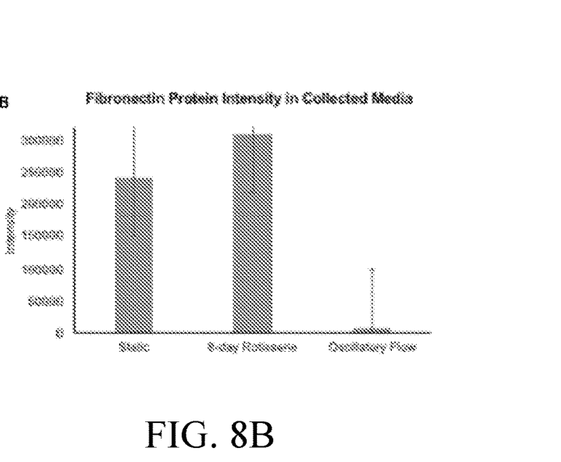

Once the media was collected form all three groups, i.e., static, 8-days rotisserie, and oscillatory flow, the protein intensity was analyzed through mass spectrometry. One protein of interest was fibronectin, which demonstrated a significantly lower ($p<0.05$) intensity of fibronectin in the oscillatory flow group compared to the static and 8-days rotisserie groups (FIG. 8B). There was no significance ($p>0.05$) between the static and 8-days rotisserie group (FIG. 8B). Lower fibronectin expression may be a sign of a healthy tissue remodeling, because fibronectin has been linked to TGF-β1 binding interaction. In turn, mechanically stimulated TGF-β1 signaling is associated with valve calcification.

These findings can be attributed to the microenvironment to which the hBM-MSCs were exposed. The physiological nature of the aortic oscillatory flow waveform that was used during the experiment was intended to mimic hemodynamic shearing forces, which occur physiologically in vivo. Shear stresses that the hBM-MSCs are exposed to play a critical role in differentiating the cells toward the endothelial phenotype. Thus, the oscillatory flow group had a higher CD31 expression (endothelial phenotype).

It is demonstrated that physiologically relevant oscillatory shear stresses alone (overall mean, time-averaged shear stress, ~7.9 dynes/cm$^2$; overall mean, oscillatory shear index, ~0.18), with the absence of solid stresses in the mechanical conditioning protocol can augment the endothelial phenotype while restricting the activated smooth muscle phenotype (a-SMA) to relatively low levels. Note that oscillatory flow is distinct from pulsatile flow in that the latter may not necessarily induce oscillations in the fluid.

The samples from the flex-flow group exhibited a valve-like distribution of cells that expressed endothelial (CD31) and myofibroblast (a-SMA) phenotypes within the surface and interstitial layers, respectively. This was likely due to the presence of oscillatory shear stresses (overall mean, OSI ~0.11) on the sample, induced during the time-varying flow on the sample surface, which was created via the cyclic flexure of the immersed samples in the steady flow environment.

In the current study, physiologically relevant, flow oscillations (overall, mean OSI ~0.18) that were directly created via the aortic flow waveform augmented the CD31 phenotype. In contrast to flex-flow conditions, however, oscillatory flow without the presence of concomitant flexural stresses served to substantially reduce the a-SMA phenotype. Therefore, physiologically relevant oscillatory flow alone can serve as a means to promote controlled in vitro valve tissue regeneration, by enhancing the endothelial phenotype while restricting myofibroblast phenotypic expression. Since a-SMA is indicative of both normal as well as pathological tissue remodeling activity, it would therefore be more prudent to minimize a-SMA expression while augmenting other valvular parameters that can be achieved via mechanical conditioning. However, since solid stresses may serve to also considerably increase a-SMA, a compromise can be achieved via the sole application of physiologically relevant oscillatory fluid-induced stresses, without structural deformation of the specimens.

Lastly, a very low level (relative to controls) of fibronectin expression found within the conditioned media of the oscillatory flow-stimulated, hBM-MSC-seeded scaffolds is suggestive of the potential for physiologically relevant oscillatory shear stresses to minimize the risk of provoking TGF-b-mediated, pathological valve remodeling activity following in vivo translation.

Example 7—Primate Surgeries

Adult *Hamadryas baboons* (n=4; all male; 8 years of age) can be separated and brought into caged housing. They will be fasted for 8 hours before surgery. They can be sedated, followed by oral intubation and placed on a respiratory ventilator under general anesthesia. A pre-operative dose of antibiotics will be given within 1 hour of incision. After induction of general endotracheal anesthesia, the animals can be prepped in a sterile fashion using a chlorhexidine-based solution.

A right thoracotomy can be performed via a limited skin incision and the thymus gland will be left in place. During the open heart surgery, when a clear and unobstructed view of the cardiac muscle is observed, local ischemia can be created within the muscle by ligation of the lateral ends of the circumflex coronary artery, until MI occurs, which will be evident by a rise in the ST-segment in the electrocardiogram recording of at least 2 mV as well as visible changes in heart contraction. These changes will also be quantified by real-time echocardiography analysis both before and after MI-induction. Next, 5 ml of IESCE can be injected onto adversely affected regions via intra-cardiac injections, with a maximum of five injection sites anticipated. A permanent tissue-staining dye will be marked at each injection site as a reference for histological evaluation at 12 months post-surgery. The animals will be monitored for 12 months using echo-cardiographic evaluation of heart function every other week (under the supervision of a cardiologist), followed by terminal histological and immunohistochemical analysis at the end of the study period. The IESCE will be prepared identically as described in Example 6, except that baboon BMSCs instead of human can be used.

A postoperative transesophageal echo can be performed, and any issues will be addressed at that time. After confirming hemostasis, the thoracotomy will be re-approximated with interrupted vicryl suture. A mediastinal chest tube will be placed prior to closing the chest. The skin and subcutaneous tissues of the chest will be closed with running layers of vicryl suture. Sterile dressings will be placed, and the animals can be returned to the recovery cage area. There, they can be given medications to be kept comfortable while awake enough to remove the breathing tube. By morning much of the sedation can be removed and the animals can be kept on pain medicine for 3-5 days. They can be allowed to feed ad lib the first day after surgery. The chest tube can be pulled the evening of surgery or morning after surgery as long as there is no bleeding. If there is ongoing bleeding, the animals can be kept appropriately sedated until the chest tube can be pulled.

Overall, three baboons can be treated with IESCE whereas 2 baboons (1 untreated (negative control) and 1 healthy baboon with no surgical procedures (positive control)) can serve as reference values during longitudinal echo monitoring. All animals can be subjected to echocardiograms the week prior to surgery, the week of surgery (if applicable) and every 2 weeks thereafter for a total study period of 12 months. The 4 baboons that can undergo surgery can be subjected to histological and immunostaining analysis after euthanasia at the end of this study period. If an aged-matched animal at the non-human primate facility unrelated to this study dies during the study period due to non-cardiac related reasons, its heart can also be assessed histologically and with immune-stains, to serve as a positive control.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

We claim:

1. Injectable enhanced stem cell exosomes (IESCE) secreted from stem cells, the IESCE being produced by a method comprising seeding stem cells onto a bio-scaffold; subjecting the stem cells on the bio-scaffold to rotisserie culture for ≥8 days; placing the bio-scaffold in a bioreactor that delivers a physiological oscillatory flow condition to the stem cells on the bio-scaffold; culturing the stem cells in a culture medium in the bioreactor under the physiological oscillatory flow condition for ≥14 days; collecting IESCEs from the culture medium; and measuring a level of fibronectin in IESCEs, wherein the level of fibronectin in the IESCE is at least 50% lower as compared to those of static culture; the stem cells being bone marrow mesenchymal stem cells (BMSCs); and the IESCE comprising at least one tissue repair factor selected from interleukin-6 (IL-6), interleukin-10 (IL-10), extracellular matrix metalloproteinase inducer (EMMPRIN), matrix metalloproteinase (MMP)-9, and granulocyte colony stimulating factor (G-CSF), and the IESCEs further comprising no alpha-2-macroglobulin.

2. The IESCE of claim 1, the physiological oscillatory flow condition having an oscillatory shear index (OSI) from 0.18 to 0.23.

3. The IESCE of claim 1, the physiological oscillatory flow condition having an OSI of 0.2.

4. The IESCE of claim 1, the method comprising seeding stem cells onto a bio-scaffold; subjecting the stem cells on the bio-scaffold to rotisserie culture for 8 days; placing the bio-scaffold in a bioreactor that delivers a physiological oscillatory flow condition to the stem cells on the bio-scaffold; culturing the stem cells in a culture medium in the bioreactor under the physiological oscillatory flow condition for 14 days; collecting IESCEs from the culture medium; and measuring a level of fibronectin in IESCEs.

5. A pharmaceutical composition comprising IESCE of claim 1 and a pharmaceutically acceptable carrier.

* * * * *